(12) United States Patent
Kwok et al.

(10) Patent No.: US 11,535,655 B2
(45) Date of Patent: *Dec. 27, 2022

(54) METHOD OF TREATING INFLAMMATORY BOWEL DISEASE

(71) Applicant: Cheer Global Limited, Hong Kong (CN)

(72) Inventors: Sui Yi Kwok, Hong Kong (CN); Norman Fung Man Wai, Vancouver (CA); Chi Shing Tai, Hong Kong (CN)

(73) Assignee: Cheer Global Limited, Hong Kong (CN)

( * ) Notice: Subject to any disclaimer, the term of this patent is extended or adjusted under 35 U.S.C. 154(b) by 15 days.

This patent is subject to a terminal disclaimer.

(21) Appl. No.: 17/247,223

(22) Filed: Dec. 4, 2020

(65) Prior Publication Data

US 2021/0171590 A1    Jun. 10, 2021

Related U.S. Application Data

(60) Provisional application No. 62/944,397, filed on Dec. 6, 2019.

(51) Int. Cl.
| | | |
|---|---|---|
| C07K 14/47 | (2006.01) | |
| A61K 45/06 | (2006.01) | |
| A61K 9/00 | (2006.01) | |
| A61P 1/00 | (2006.01) | |
| A61K 38/00 | (2006.01) | |

(52) U.S. Cl.
CPC ............ *C07K 14/47* (2013.01); *A61K 9/0019* (2013.01); *A61K 45/06* (2013.01); *A61P 1/00* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 9,138,464 B2 * | 9/2015 | Winslow | A61P 9/00 |
| 10,752,672 B1 * | 8/2020 | Kwok | C07K 14/805 |
| 2016/0022783 A1 * | 1/2016 | Malavalli | A61P 9/04 |
| | | | 514/13.5 |

FOREIGN PATENT DOCUMENTS

| | | |
|---|---|---|
| CN | 1322761 A | 11/2001 |
| CN | 106573056 A | 4/2017 |

OTHER PUBLICATIONS

"Capital Digestive Care" (downloaded on Nov. 25, 2021 from URL:< Ulcerative Colitis Treatment & Prevention Ijamsville, Laurel & Olney, MD—Capital Digestive Care>) (Year: 2021).*
"Women's health.gov", U.S. Department of Health and Human Services, Office on Women's Health (Year: 2013).*
Baik et al., J Korean Soc Coloproctol 2012;28(3):121-131 (Year: 2012).*
Orholm et al., N Engl J Med 1991; 324:84-88 (Year: 1991).*
Nemes et al. (Rev Med Chir Soc Med Nat Iasi Jan.-Mar. 2016;120(1):34-9) (Year: 2016).*
Looker et al. (Nature. Mar. 19, 1992;356(6366):258-60) (Year: 1992).*
"PDB: 1O1I-A" (Chain A, Hemoglobin alpha chain, Nov. 19, 2002) (Year: 2002).*
"PDB: 1O1O-B" (Chain B, Hemoglobin beta chain, Nov. 17, 2002) (Year: 2002).*
Cummins et al. (Microbes and Infection 19 (2017) 210e221) (Year: 2017).*
Kaitha et al. (World J Gastrointest Pathophysiol Aug. 15, 2015; 6(3): 62-72) (Year: 2015).*
International Search Report and Written Opinion of PCT application No. PCT/CN2020/133825 issued from the International Search Authority dated Mar. 3, 2021.
Chain A, Hemoglobin Alpha chain PDB: 101J_A Jul. 26, 2019.
Chain B, Hemoglobin (Val Beta1 Met) Mutant PDB: 1A0U_B Oct. 10, 2012.

* cited by examiner

*Primary Examiner* — Sergio Coffa
(74) *Attorney, Agent, or Firm* — S&F/WEHRW

(57) ABSTRACT

Provided herein is a method for treating an inflammatory bowel disease in a subject in need thereof, the method comprising administering a therapeutically effective amount of a hemoglobin to the subject.

11 Claims, 21 Drawing Sheets

Specification includes a Sequence Listing.

Vehicle, YQ23-LD, YQ23-MD, YQ23-HD or TMB-1, i.p.

Days 0 1 2 3 4 5 6 7

H$_2$O or 2.5% DSS

| Group | Treatment 1 | Treatment 2 | No. of mice |
|---|---|---|---|
| 1 | H$_2$O | Control - Uninduced | 3 |
| 2 | 2.5% DSS | Vehicle | 4 |
| 3 | | YQ23-LD (800mg/kg YQ23) | 5 |
| 4 | | YQ23-MD (1000mg/kg YQ23) | 5 |
| 5 | | YQ23-HD (1500mg/kg YQ23) | 5 |
| 6 | | TMB-1 (1000mg/kg TMB-1) | 5 |

| Treatment 1 | H₂O (Control) Uninduced | 2.5% DSS | | | | |
|---|---|---|---|---|---|---|
| Treatment 2 | Vehicle | Vehicle | YQ23-LD | YQ23-MD | YQ23-HD | TMB-1 |
| Average colon length (cm) | 7.53 | 5.98 | 5.92 | 6.58 | 6.94 | 6.04 |
| % difference compared with 2.5% DSS + vehicle | | | -0.92% | +10.13% | +16.15% | +1.09% |

FIG. 2E (Continued)

| Group | No. of mice | Treatment 1 | Treatment 2 | Record |
|---|---|---|---|---|
| Uninduced | 5 | $H_2O$ | Vehicle; i.v. | Daily<br>1. Body weight<br>2. DAI score |
| DSS | 5 | 2.5% DSS | Vehicle; i.v. | |
| YQ23-MD | 5 | 2.5% DSS | 1000 mg/kg YQ23; i.v. | |
| YQ23-HD | 5 | 2.5% DSS | 1500 mg/kg YQ23; i.v. | |
| TBM-1-HD | 5 | 2.5% DSS | 1500 mg/kg TBM-1; i.v. | | di-alpha chain (SEQ ID NO: 1)

MLSPADKTNVKAAWGKVGAHAGEYGAEAFERMFLSFPTTKTYFPHFDLSHGSAQVKGQGKKVADALTNAV
AHVDDMPNALSALSDLHAHKLRVDPVNFKLLSHCLLVTLAAHLPAEFTPAVHASLDKFLASVSTVLTSKYRGM
LSPADKTNVKAAWGKVGAHAGEYGAEAFERMFLSFPTTKTYFPHFDLSHGSAQVKGQGKKVADALTNAVA
HVDDMPNALSALSDLHAHKLRVDPVNFKLLSHCLLVTLAAHLPAEFTPAVHASLDKFLASVSTVLTSKYR

FIG. 5 beta chain for TBM1 (SEQ ID NO: 2)

MHLTPEEKSAVTALWGKVNVDEVGGEALGRLLVVYPWTQRFFESFGDLSTPDAVMGNPKVKAHGKKVLGA
FSDGLAHLDNLKGTFATLSELHCDKLHVDPENFRLLGNVLVCVLAHHFGKEFTPPVQAAYQKVVAGVANALA
HKYH

FIG. 6

SEQUENCE LISTING

<160> NUMBER OF SEQ ID NOS: 2

<210> SEQ ID NO 1
<211> LENGTH: 283
<212> TYPE: PRT
<213> ORGANISM: Artificial Sequence
<220> FEATURE:
<223> OTHER INFORMATION: Di-alpha chain recombinant protein, prepared in the lab

<400> SEQUENCE: 1

Met Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Phe Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly Gln Gly Lys Lys Val Ala Asp
    50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg Gly Met Leu
    130                 135                 140

Ser Pro Ala Asp Lys Thr Asn Val Lys Ala Ala Trp Gly Lys Val Gly
145                 150                 155                 160

Ala His Ala Gly Glu Tyr Gly Ala Glu Ala Phe Glu Arg Met Phe Leu
                165                 170                 175

Ser Phe Pro Thr Thr Lys Thr Tyr Phe Pro His Phe Asp Leu Ser His
            180                 185                 190

Gly Ser Ala Gln Val Lys Gly Gln Gly Lys Lys Val Ala Asp Ala Leu
        195                 200                 205

Thr Asn Ala Val Ala His Val Asp Asp Met Pro Asn Ala Leu Ser Ala
    210                 215                 220

Leu Ser Asp Leu His Ala His Lys Leu Arg Val Asp Pro Val Asn Phe
225                 230                 235                 240

Lys Leu Leu Ser His Cys Leu Leu Val Thr Leu Ala Ala His Leu Pro
                245                 250                 255

Ala Glu Phe Thr Pro Ala Val His Ala Ser Leu Asp Lys Phe Leu Ala
            260                 265                 270

Ser Val Ser Thr Val Leu Thr Ser Lys Tyr Arg
        275                 280

<210> SEQ ID NO 2
<211> LENGTH: 146
<212> TYPE: PRT
<213> ORGANISM: Artificial Sequence
<220> FEATURE:
<223> OTHER INFORMATION: Beta chain recombinant protein, prepared in the lab

<400> SEQUENCE: 2

Met His Leu Thr Pro Glu Glu Lys Ser Ala Val Thr Ala Leu Trp Gly

```
1               5                   10                  15
Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
            35                  40                  45

Ser Thr Pro Asp Ala Val Met Gly Asn Pro Lys Val Lys Ala His Gly
        50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
            115                 120                 125

Ala Tyr Gln Lys Val Val Ala Gly Val Ala Asn Ala Leu Ala His Lys
        130                 135                 140

Tyr His
145
```

METHOD OF TREATING INFLAMMATORY BOWEL DISEASE

CROSS-REFERENCE TO RELATED APPLICATIONS

This application claims the benefit of priority of U.S. Provisional Application No. 62/944,397, filed on Dec. 6, 2019, the contents of which are hereby incorporated by reference in their entirety for all purposes.

TECHNICAL FIELD

The present disclosure generally relates to methods for treating inflammatory bowel disease.

BACKGROUND

Inflammatory bowel disease (IBD), comprising ulcerative colitis (UC) and Crohn's disease (CD), is a chronic and relapsing gastrointestinal inflammatory disease. Traditionally, the prevalence and incidence rate of IBD is high in North America and Western Europe, and over 3.5 million people suffer from IBD in these regions. Increasing epidemiology studies suggest that the incidence of IBD may be rapidly increasing in developing countries and areas where IBD was previously uncommon, such as South America, Eastern Europe, Asia, and Africa. With a sustained high incidence rate in different countries, IBD has become an emerging disease worldwide.

As an idiopathic disease, the exact etiology for IBD remains to be elucidated. Nevertheless, interactions between causal factors—environment, host genetics, immune system and microbiome—are known to be important. Therefore, the treatment goals for IBD are to induce and maintain remission of symptoms and mucosal inflammation. Currently, the major treatment option for IBD is 5-aminosalicylic acid (5-ASA) and corticosteroids, however, significant side effects including headaches, vomiting, diarrhea, and pancreatic and kidney problems have been reported. As such, new therapeutic agents with high efficacy and low toxicity are urgently needed for the treatment of IBD.

SUMMARY

Herein, the in vivo anti-inflammatory effect of hemoglobin, e.g., YQ23 (cross-linked tetrameric bovine hemoglobin) and TMB-1 (recombinant hemoglobin comprising a di-alpha chain and two beta chains, wherein the di-alpha chain consist of SEQ ID NO: 1 and the each of the two beta chains consist of SEQ ID NO: 2), in the DSS-induced acute colitis mouse model are presented. The results provide data on the efficacy of YQ23 & TBM-1, which demonstrate the use of hemoglobin as an anti-inflammatory drug.

In a first aspect, provided herein is a method for treating an inflammatory bowel disease in a subject in need thereof, the method comprising administering a therapeutically effective amount of a hemoglobin to the subject.

In a first embodiment of the first aspect, provided herein is the method of the first aspect, wherein the inflammatory bowel disease is selected from the group consisting of ulcerative colitis (UC), indeterminate colitis, Crohn's disease (CD), lymphocytic colitis, microscopic colitis, collagenous colitis, autoimmune enteropathy, allergic gastrointestinal disease, and eosinophilic gastrointestinal disease.

In a second embodiment of the first aspect, provided herein is the method of the first aspect, wherein the inflammatory bowel disease is selected from the group consisting of UC, CD, and indeterminate colitis.

In a third embodiment of the first aspect, provided herein is the method of the first aspect, wherein the inflammatory bowel disease is CD.

In a fourth embodiment of the first aspect, provided herein is the method of the first aspect, wherein the inflammatory bowel disease is UC.

In a fifth embodiment of the first aspect, provided herein is the method of the first aspect, wherein the subject has a circulating hemoglobin concentrations between 12-15 g/dl or greater.

In a sixth embodiment of the first aspect, provided herein is the method of the first aspect, wherein the hemoglobin is administered intraperitoneally.

In a seventh embodiment of the first aspect, provided herein is the method of the first aspect, wherein the hemoglobin is administered intravenously.

In an eighth embodiment of the first aspect, provided herein is the method of the first aspect, wherein the hemoglobin has a p50 greater than 24 mm Hg.

In a ninth embodiment of the first aspect, provided herein is the method of the first aspect, wherein the hemoglobin has a p50 greater than 30 mm Hg.

In a tenth embodiment of the first aspect, provided herein is the method of the first aspect, wherein the hemoglobin is bovine, human, canine, porcine, or equine hemoglobin.

In a eleventh embodiment of the first aspect, provided herein is the method of the first aspect, wherein the hemoglobin is a naturally occurring hemoglobin, a modified hemoglobin, a recombinant hemoglobin, or a modified recombinant hemoglobin.

In a twelfth embodiment of the first aspect, provided herein is the method of the first aspect, wherein the hemoglobin is a crosslinked hemoglobin or a recombinant hemoglobin.

In a thirteenth embodiment of the first aspect, provided herein is the method of the first aspect, wherein the hemoglobin is a non-polymeric crosslinked hemoglobin or a recombinant hemoglobin comprising a di-alpha chain and two beta chains.

In a fourteenth embodiment of the first aspect, provided herein is the method of the first aspect, wherein the hemoglobin is a non-polymeric fumaryl crosslinked bovine hemoglobin.

In a fifteenth embodiment of the first aspect, provided herein is the method of the first aspect, wherein the hemoglobin is a recombinant hemoglobin comprising a di-alpha chain and two beta chains, wherein the di-alpha chain comprises a polypeptide sequence having at least 98.93% sequence homology with SEQ ID NO: 1; and each of the two beta chains comprise a polypeptide sequence having at least 97.94% sequence homology with SEQ ID NO: 2.

In a sixteenth embodiment of the first aspect, provided herein is the method of the fifteenth embodiment of the first aspect, wherein the inflammatory bowel disease is selected from the group consisting of UC, CD, and indeterminate colitis; and the hemoglobin has a p50 between 30-50 mm Hg.

In a seventeenth embodiment of the first aspect, provided herein is the method of the fifteenth embodiment of the first aspect, wherein the inflammatory bowel disease is selected from the group consisting of UC, CD, and indeterminate colitis; and the hemoglobin has a p50 between 20-30 mm Hg.

In a eighteenth embodiment of the first aspect, provided herein is the method of the seventeenth embodiment of the first aspect, wherein the recombinant hemoglobin comprising a di-alpha chain and two beta chains, wherein the di-alpha chain comprises a polypeptide sequence consisting of SEQ ID NO: 1; and each of the two beta chains comprise a polypeptide sequence consisting of SEQ ID NO: 2.

In a nineteenth embodiment of the first aspect, provided herein is the method of the first aspect, further comprising co-administering a therapeutically effective amount of at least one agent to the subject, wherein the at least one agent is selected from the group consisting of an anti-inflammatory agent and an antibacterial agent.

BRIEF DESCRIPTION OF THE DRAWINGS

It should be understood that the drawings described herein are for illustration purposes only. The drawings are not necessarily to scale, with emphasis generally being placed upon illustrating the principles of the present teachings. The drawings are not intended to limit the scope of the present disclosure in any way.

FIG. 5 depicts the polypeptide sequence of the di-alpha globin chain (SEQ ID NO: 1) of TMB-1.

FIG. 6 depicts the polypeptide sequence of the beta globin chain (SEQ ID NO: 2) of TMB-1.

DETAILED DESCRIPTION

Definitions

Figures 1A, 1B:
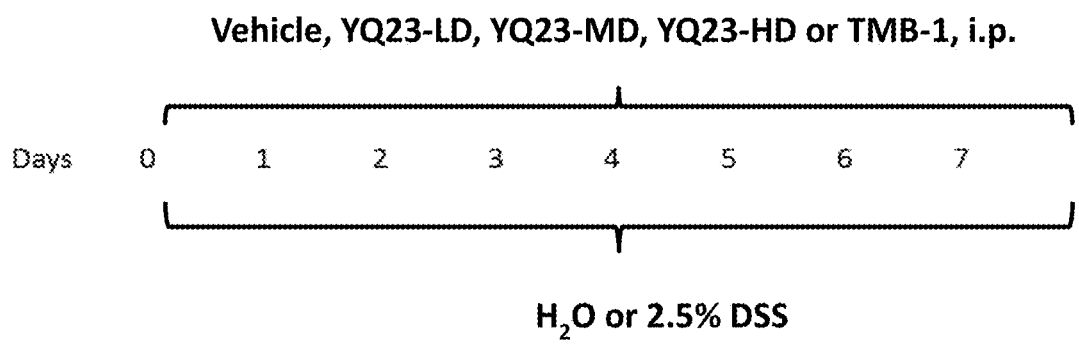
FIG. 1A depicts an exemplary treatment regimen according to certain embodiments described herein (i.p. injection experiment).
FIG. 1B depicts a table showing dosage amounts of YQ23 and TMB-1 for experiments described below (i.p. injection experiment).

The term "recombinant hemoglobin(s)" as used herein indicates a hemoglobin molecule and/or its variant with a molecular size of at least approximately 65 kDa and is synthesized by an γ standard molecular biology techniques rather than being isolated or purified from any animal or human source.

The term "protein" or "polypeptide" as used herein indicates an organic polymer composed of two or more amino acid monomers and/or analogs thereof. The term "polypeptide" includes amino acid polymers of any length including full length proteins and peptides, as well as analogs and fragments thereof. A polypeptide of three or more amino acids is also called an oligopeptide. As used herein, the term "amino acid", "amino acid monomer", or "amino acid residue" refers to any of the twenty naturally occurring amino acids including synthetic amino acids with unnatural side chains and including both D and L optical isomers. The terms "amino acid analog" and "analog" that are used interchangeably refer to an amino acid in which one or more individual atoms have been replaced, either with a different atom, isotope, or with a different functional group but is otherwise identical to its natural amino acid analog and have similar chemical and/or physical properties to its natural amino acid analog.

As used herein, the term "variant" refers to a polypeptide or polynucleotide sequence differing from a reference polypeptide or polynucleotide sequence by at least one conservative amino acid substitution and/or by at least one non-conservative amino acid substitution, but retaining essential properties thereof. Generally, variants are overall closely similar, and, in many regions, identical to the reference polypeptide or polynucleotide sequence A variant can, for example, comprise the amino acid sequence of the parent polypeptide sequence with at least one conservative amino acid substitution. Alternatively or additionally, the variant can comprise the amino acid sequence of the parent polypeptide sequence with at least one non-conservative amino acid substitution. In this case, it is preferable for the non-conservative amino acid substitution to not interfere with or inhibit the biological activity of the functional variant. The non-conservative amino acid substitution may enhance the biological activity of the variant, such that the biological activity of the variant is increased as compared to the parent polypeptide.

The term "amino acid modification" as used herein indicates amino acid insertion, substitution, or deletion, etc. Amino acid substitutions of the described polypeptides can be conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, le, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., lie, Thr, and Val), an amino acid with an aromatic side-chain substituted for another amino acid with an aromatic side chain (e.g., His, Phe, Trp, and Tyr), etc.

The term "nucleotide modifications" as used herein refers to nucleotide insertion, substitution, deletion, etc.

The term "percentage sequence homology", when used in reference to a polypeptide or polynucleotide sequence, refers to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions for the longer sequence in the window of comparison and multiplying the result by 100 to yield the percentage of sequence homology. Homology is evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman, 1988, Proc. Natl. Acad. Sci. USA 85(8):2444-2448; Altschul et al., 1990, J. Mol. Biol. 215(3):403-410; Thompson et al., 1994, Nucleic Acids Res. 22(2):4673-4680; Higgins et al. 1996, Methods Enzymol. 266:383-402; Altschul et al., 1990, J. Mol. Biol. 215(3):403-410; Altschul et al., 1993, Nature Genetics 3:266-272). In certain embodiments, protein and nucleic acid sequence homologies are evaluated using the Basic Local Alignment Search Tool ("BLAST") which is well known in the art (see, e.g., Karlin and Altschul, 1990, Proc. Natl. Acad. Sci. USA 87:2267-2268; Altschul et al., 1990, J. Mol. Biol. 215:403-410; Altschul et al., 1993, Nature Genetics 3:266-272; Altschul et al., 1997, Nuc. Acids Res. 25:3389-3402).

As used herein, the term "isolated" in connection with a compound described herein means the compound is not in a cell or organism and the compound is separated from some or all of the components that typically accompany it in a cell or organism.

As used herein, the term "substantially pure" in connection with a sample of a compound described herein means the sample contains at least 60% by weight of the compound. In certain embodiments, the sample contains at least 70% by weight of the compound; at least 75% by weight of the compound; at least 80% by weight of the compound; at least 85% by weight of the compound; at least 90% by weight of the compound; at least 95% by weight of the compound; or at least 98% by weight of the compound.

As used herein, the term "substantially stroma-free" in connection with a sample of a compound described herein means the sample contains less than 5% by weight stroma. In certain embodiments, the samples contains less than 4% by weight stroma; less than 3% by weight stroma; less than 2% by weight stroma; less than 1% by weight stroma; less than 0.5% by weight stroma; less than 0.1% by weight stroma; less than 0.05% by weight stroma; or less than 0.01% by weight stroma.

As used herein, the terms "treat", "treating", "treatment", and the like refer to reducing or ameliorating a disorder and/or symptoms associated therewith. It will be appreciated, although not precluded, treating a disorder or condition does not require that the disorder, condition, or symptoms associated therewith be completely eliminated.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "therapeutically effective amount" as used herein, means that amount of the therapeutic or pharmaceutical agent that elicits a biological, medicinal, or imaging response in a cell culture, tissue system, subject, animal, or human that is being sought by a researcher, veterinarian, clinician, or physician, which includes alleviation of the symptoms of the disease, condition, or disorder being treated.

The term "subject" as used herein, refers to an animal, typically a mammal or a human, that will be or has been the object of treatment, observation, and/or experiment. When the term is used in conjunction with administration of a compound described herein, then the subject has been the object of treatment, observation, and/or administration of the compound described herein.

The term "a p50 value" as used herein indicates the oxygen tension at which hemoglobin is 50% saturated. Values of p50 are negatively correlated with substrate affinity; lower values correspond to higher affinity and vice versa.

Provided herein is a method for treating an inflammatory bowel disease in a subject in need thereof comprising the step of administering a therapeutically effective amount of a hemoglobin to the subject.

The subject may suffer from an inflammatory bowel disease selected rom Crohn's disease (CD), gastroduodenal Crohn's disease, ulcerative colitis (UC), indeterminate colitis, collagenous colitis, diverticulitis, Behcet's disease, microalborne colitis, ulcerative rectalitis, sinusitis, left colitis, total colitis, ileocolic colitis, ileitis, lymphocytic colitis, microscopic colitis, autoimmune enteropathy, allergic gastrointestinal disease, eosinophilic gastrointestinal disease, and undefined colitis. CD and UC are the two most common forms of IBD. IBD is an autoimmune disease of the digestive system. CD can be present in any part of the gastrointestinal tract, including the terminal ileum, and can affect all cell types of the gastrointestinal tract. UC is generally limited to the colon and rectum, and typically affects only mucosal cells.

Any type of hemoglobin can be used in connection with the methods described herein. The hemoglobin may be naturally occurring hemoglobin, modified hemoglobin, recombinant hemoglobin, or modified recombinant hemoglobin. In certain embodiments, the hemoglobin is derived from bovine, human, canine, porcine, equine blood, hemoglobin, or a subunit thereof. In certain embodiments, the hemoglobin is isolated from blood or produced transgenically.

The hemoglobin may be isolated, substantially pure, and/or substantially stroma free.

Modified hemoglobin useful in connection with the methods described herein include hemoglobin with one or more modifications selected from the group consisting of PEGylation and intramolecular and/or intermolecular crosslinking (e.g., with glutaraldehyde, sebacyl, fumaryl, succinyl, trimesyl and the like).

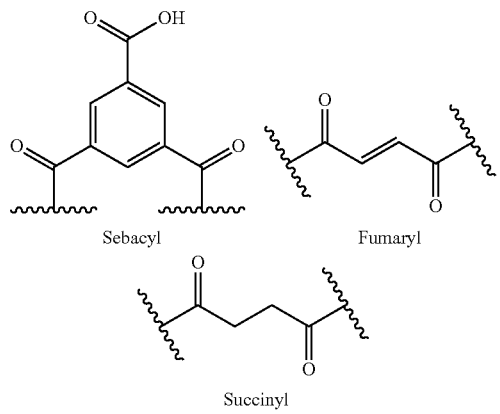

The recombinant hemoglobin can be a naturally occurring hemoglobin or include one or more mutations, such as one or more amino acid substitutions, deletions, or additions, or covalent linking globin subunits (e.g., resulting in a di-α globin subunit and/or di-β globin subunit). In certain embodiments, the hemoglobin is recombinant hemoglobin comprising a di-alpha chain and two beta chains.

The di-alpha chain can comprises a polypeptide sequence having at least 98.93% sequence homology with SEQ ID NO: 1, wherein the amino acids at position 1 and position 143 of SEQ ID NO: 1 must be methionine, the amino acids at position 29 and position 171 of SEQ ID NO: 1 must be phenylalanine, and the amino acids at position 58 and position 200 of SEQ ID NO: 1 must be glutamine.

The di-alpha chain can comprise a polypeptide sequence having at least 98.93% sequence homology with SEQ ID NO: 1. Polypeptides having at least 98.93% sequence homology to SEQ ID NO: 1 can refer to polypeptides having at most three amino acid modifications, i.e. zero, one, two, or three amino acid modifications with respect to the SEQ ID NO: 1. In certain embodiments, the di-alpha chain comprises a polypeptide sequence having at least 99.29% sequence homology with the SEQ ID NO: 1. Polypeptides having at least 99.29% sequence homology can have at most two amino acid modifications, i.e. zero, one, or two amino acid modifications with respect to the SEQ ID NO: 1. In certain embodiments, the di-alpha chain comprises a polypeptide sequence having at least 99.64% sequence homology with the SEQ ID NO: 1. Polypeptides having at least 99.64% sequence homology can have at most one amino acid modifications, i.e. zero or one amino acid modification with respect to the SEQ ID NO: 1. In certain embodiments, the di-alpha chain comprises a polypeptide sequence of SEQ ID NO: 1. In certain embodiments, the di-alpha chain consists of a polypeptide sequence of SEQ ID NO: 1. The one, two, or three amino acid modifications can occur at any amino acid present in SEQ ID NO: 1, except the positions 1, 29, 58, 143, 171, and 200 of SEQ ID NO: 1, in which position 1 and position 143 of SEQ ID NO: 1 must be methionine, the amino acids at position 29 and position 171 of SEQ ID NO: 1 must be phenylalanine, and the amino acids at position 58 and position 200 of SEQ ID NO: 1 must be glutamine.

Each of the two beta chains can comprise a polypeptide sequence having at least 97.94% sequence homology with SEQ ID NO: 2. Polypeptides having at least 97.94% sequence homology can have at most three amino acid modifications, i.e. zero, one, two, or three amino acid modifications with respect to the SEQ ID NO: 2. In certain embodiments, each of the two beta chains comprises a polypeptide sequence having at least 98.63% sequence homology with the SEQ ID NO: 2. Polypeptides having at least 98.63% sequence homology can have at most two amino acid modifications, i.e. zero, one, or two amino acid modifications with respect to the SEQ ID NO: 2. In certain embodiments, each of the two beta chains comprises a polypeptide sequence having at least 99.31% sequence homology with the SEQ ID NO: 2. Polypeptides having at least 99.31% sequence homology can have at most one amino acid modifications, i.e. zero or one amino acid modification with respect to the SEQ ID NO: 2. In certain embodiments, each of the two beta chains comprises a polypeptide sequence of SEQ ID NO: 2. In certain embodiments, the one, two, or three amino acid modifications can occur at any amino acid present in SEQ ID NO: 2, except the position 1 of the SEQ ID NO: 2, which must be methionine.

In certain embodiments, the hemoglobin is a recombinant hemoglobin described in U.S. Pat. No. 10,752,672, which is hereby incorporated by reference in its entirety.

In certain embodiments, the hemoglobin is a recombinant hemoglobin comprising a di-alpha chain and two beta chains, wherein the di-alpha chain comprise SEQ ID NO: 1 and the each of the two beat chains comprise SEQ ID NO: 2. In certain embodiments, the hemoglobin is recombinant hemoglobin comprising a di-alpha chain and two beta chains, wherein the di-alpha chain consist of SEQ ID NO: 1 and the each of the two beta chains consist of SEQ ID NO: 2.

In certain embodiments, the hemoglobin is a modified hemoglobin is a fumaryl crosslinked non-polymeric hemoglobin. In certain embodiments, the fumaryl crosslinked non-polymeric hemoglobin comprises one or more fumaryl crosslinks. In certain embodiments, the fumaryl crosslinked non-polymeric hemoglobin is heat treated.

In certain embodiments, the modified hemoglobin is an α-α fumaryl crosslinked hemoglobin described in U.S. Pat. Nos. 7,932,356 and 8,048,856, which are hereby incorporated by reference in their entirety.

In certain embodiments, the modified hemoglobin is a fumaryl crosslinked hemoglobin comprising greater than 10%, greater 20%, greater than 30%, greater 40%, or greater than 50% α-α crosslinking. In certain embodiments, the modified hemoglobin is a fumaryl crosslinked bovine hemoglobin having between 10-60%; 10-70%; 10-50%, 10-40%, 10-30%, or 10-20% α-α crosslinking.

In certain embodiments, the modified hemoglobin is an β-β fumaryl crosslinked hemoglobin described in U.S. Pat. No. 8,106,011, which is hereby incorporated by reference in their entirety.

In certain embodiments, the modified hemoglobin is a fumaryl crosslinked bovine hemoglobin comprising greater than 10%, greater 20%, greater than 30%, greater 40%, or greater than 50% β-β crosslinking. In certain embodiments, the modified hemoglobin is a fumaryl crosslinked bovine hemoglobin having between 10-60%; 10-70%; 10-50%; 10-40%, 10-30%, or 10-20% β-β crosslinking.

The hemoglobin can have any p50 value. In certain embodiments, the p50 value is between 10 and 50; 20 and 50; 30 and 50; 20 and 45; or 20 and 40; or 40 and 50 mmHg.

Alternatively, red blood cells can be administered in place of hemoglobin to the subject in the methods described herein.

The mode of administration for the hemoglobin herein may be any suitable route that delivers the agent to the subject, such as parenteral administration, e.g., intradermal, intramuscular, intraperitoneal, intravenous or subcutaneous, pulmonary; transmucosal (oral, intranasal, intravaginal, rectal); using a formulation in a tablet, capsule, solution, suspension, powder, gel, particle; and contained in a syringe, an implanted device, osmotic pump, cartridge, micropump; or other means appreciated by the skilled artisan, as well known in the art. Site specific administration may be achieved by for example intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery. In certain embodiments, the hemoglobin is administered to the subject intraperitoneally.

Optimal dosages and dosage regimens to be administered may be readily determined by those skilled in the art, and will vary with the mode of administration, the strength of the preparation and the advancement of the disease condition. In addition, factors associated with the particular patient being treated, including patient's sex, age, weight, diet, physical activity, time of administration and concomitant diseases, will result in the need to adjust dosages and/or regimens. In certain embodiments, the hemoglobin is administered to the subject on a once daily, once weekly, twice weekly, thrice weekly, once monthly, or twice monthly basis.

In certain embodiments, the method for treating an inflammatory bowel disease in a subject in need thereof comprises the step of co-administering a therapeutically effective amount of a hemoglobin and a therapeutically effective amount of an anti-inflammatory agent to the subject.

The anti-inflammatory agent can be any anti-inflammatory agent known in the art. In certain embodiments, the anti-inflammatory agent is any anti-inflammatory agent useful in the treatment of IBD or IBS. Exemplary anti-inflammatory agents include nonsteroidal anti-inflammatory drugs (NSAID), corticosteroids, antibiotics, immune modifying agents, and biologic families. Exemplary anti-inflammatory agents include, but are not limited to, an aminosalcylate, such as 5-aminosalcylic acid, sulfasalazine, balsalazide, olsalazine, a steroid, such as budesonide, dexamethasone (e.g., 21-acetate), betamethasone (e. G., 17-valerate), thixocortol pivalate, triamcinolone, triamcinolone Acetonide 21-palmitate, diacetate or hexasatonide), mometasone, amcinonide, desonide, fluorocinonide, hascinonide, fluorocortolone, hydrocortisone, fluticasone propionate, and methylprednisolone; an immunosuppressive agent, such as tacrolimus, azathioprine, mitoxantrone, cyclophosphamide, mycophenolate mopetil or rapamycin; and a TNF antagonist, such as infliximab and adalimumab.

In certain embodiments, the method for treating an inflammatory bowel disease in a subject in need thereof further comprises co-administering a therapeutically effective amount of an antibacterial agent to the subject.

Any antibacterial agent that is conventionally used for IBD may be used. The selection of the appropriate antibacterial agent is well within the skill of a person of ordinary skill in the art. Exemplary antibacterial agents include, but are not limited to, penicillin, cephalosporin, polyamicin, rifampicin, lipamammine (pidacommaicin), quinolone, sulphonamide, Lipopeptides, glycinates, and oxindole.

The hemoglobin described herein can be administered according to therapeutic protocols well known in the art. It will be apparent to those skilled in the art that the administration of the hemoglobin described herein and the anti-inflammatory agent can be varied depending on the disease being treated and the known effects of the anti-inflammatory agent on that disease. Also, in accordance with the knowledge of the skilled clinician, the therapeutic protocols (e.g., dosage amounts and times of administration) can be varied in view of the observed effects of the administered therapeutic agents (i.e., anti-inflammatory agent) on the subject, and in view of the observed responses of the disease to the administered hemoglobin.

Also, in general, the hemoglobin and the anti-inflammatory agent and/or the antibacterial agent do not have to be administered in the same pharmaceutical composition, and may, because of different physical and chemical characteristics, have to be administered by different routes. For example, the hemoglobin described herein may be administered intravenously to generate and maintain good blood levels, while the anti-inflammatory agent may and/or the antibacterial agent be administered orally. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of the anti-inflammatory agent and/or antibacterial agent will depend upon the diagnosis of the attending physicians and their judgment of the condition of the patient and the appropriate treatment protocol.

The hemoglobin and the anti-inflammatory agent and/or antibacterial agent may be administered concurrently (e.g., simultaneously, essentially simultaneously or within the same treatment protocol) or sequentially, depending upon the nature of the inflammatory bowel disease, the condition of the patient, and the actual choice of anti-inflammatory agent and/or antibacterial agent to be administered in conjunction (i.e., within a single treatment protocol) with the hemoglobin.

If the hemoglobin and the anti-inflammatory agent and/or antibacterial agent are not administered simultaneously or essentially simultaneously, then the optimum order of administration of the hemoglobin and the anti-inflammatory agent and/or antibacterial agent, may be different for different diseases or conditions. Thus, in certain situations the hemoglobin may be administered first followed by the administration of the anti-inflammatory agent and/or antibacterial agent; and in other situations the anti-inflammatory agent and/or antibacterial agent may be administered first followed by the administration of the hemoglobin. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the anti-inflammatory agent and/or antibacterial agent may be administered first and then the treatment continued with the administration of the hemoglobin followed, where determined advantageous, by the administration of the anti-inflammatory agent and/or antibacterial agent, and so on until the treatment protocol is complete.

Thus, in accordance with experience and knowledge, the practicing physician can modify each protocol for the administration of a component (hemoglobin and anti-inflammatory agent and/or antibacterial agent) of the treatment according to the individual patient's needs, as the treatment proceeds.

In certain embodiments, the subject is a canine, feline, bovine, equine, non-human primate, or human. In certain embodiments, the subject is a human.

In certain embodiments, the subject is not suffering from or is otherwise in need of a blood transfusion, e.g., due to blood loss from trauma. The subject can have circulating hemoglobin concentrations of 12 g/dl or higher for adult women or 13 g/dl or higher for adult men or greater than 100 g/l or greater than 70 to 80 g/L. In certain embodiments, the subject has a circulating hemoglobin concentration between than 11-15 g/dl; 12-15 g/dl, 12-14 g/dl, 13-14 g/dl, or greater.

Materials and Method

YQ23 is a stabilized non-polymeric α-α fumaryl cross-linked tetrameric bovine hemoglobin (65 kDa) with undetectable/low level of dimeric hemoglobin (32 kDa), phospholipid, DNA impurities and protein impurities. The concentration of YQ23 can be about 10 g/dL and its pH range is the range of 7.4-8.4. The osmolality and viscosity (at 37° C.) can be 250-340 mosmol/kg and >0.9 centipoise, respectively. The p50 value of YQ23 is ~40 mmHg. YQ23 and its preparation are described in U.S. Pat. Nos. 7,932,356 and 8,048,856.

TBM-1 is a recombinant human hemoglobin comprising a di-α globin subunit (SEQ ID NO: 1) and two β globin subunits (SEQ ID NO: 2). The p50 value of TBM-1 is ~25 mmHg. TBM-1 and its preparation are described in U.S. Pat. No. 10,752,672.

Animal Study

Male and female wild-type C57BL/6J mice were purchased from the Jackson Laboratory (Bar Harbor, Me., USA) and were mated to maintain an inbred breeding colony at the Animal Facilities. All mice were kept in a barrier-sustained animal house, air-conditioned at 20±2° C. and humidity at 55±10%, under a 12-h light/dark cycle. Food and water were available adlibitum.

DSS-Induced Acute Colitis and Assessment (1) Drug Administration—Intraperitoneal Injection The acute colitis animal study was performed as described previously, with minor modifications [Wong, W. Y., et al., *Proteomic profiling of dextran sulfate sodium induced acute ulcerative colitis mice serum exosomes and their immunomodulatory impact on macrophages*. Proteomics, 2016. 16(7): p. 1131-45]. 8-week-old male wild type C57BL/6J mice were randomly assigned into 6 groups (n=4-5 per group) and acute colitis were induced in mice by providing 2.5% w/v DSS (reagent grade; 36 000-50 000 Da; MP Biomedicals, Solon, Ohio, USA) in drinking water. Mice were treated with vehicle, YQ23-LD (800 mg/kg), YQ23-MD (1000 mg/kg), YQ23-HD (1000 mg/kg), or TMB-1 (1000 mg/kg) by intraperitoneal injection daily for 7 consecutive days. An uninduced control group (n=3) treated with vehicle was also included. Body weight, food and water consumption were recorded daily. DAI was determined as previously described [Wong, W. Y., et al, *Gynostemma pentaphyllum saponins attenuate inflammation in vitro and in vivo by inhibition of NF-kappaB and STAT3 signaling*. Oncotarget, 2017. 8(50): p. 87401-87414]. The DAI scoring system is the sum of scores for weight loss, stool consistency and visible blood in feces (Weight loss: 0—no weight loss, 1—1-5%, 2—6-10%, 3—11-20%, 4—<20%; stool consistency: 0—normal, 2—loose, 4—diarrhea; visible blood in feces: 0—none, 2—slight bleeding, 4—gross bleeding). Mice were sacrificed at day 7, intestines were removed and colon lengths were measured. Colons were then washed with PBS, fixed in formalin solution and histological analysis was performed using H&E staining as described [Tai, W. C., et al., *Mechanistic study of the anti-cancer effect of Gynostemma pentaphyllum saponins in the Apc(Min/+) mouse model*. Proteomics, 2016. 16(10): p. 1557-69].

(2) Drug Administration—Intravenous Injection 8-week-old male wild type C57BL/6J mice were randomly assigned into 5 groups (n=5 per group) and acute colitis were induced in mice by providing 2.5% w/v DSS in drinking water. Mice were treated with vehicle, YQ23-MD (1000 mg/kg), YQ23-HD (1500 mg/kg), or TMB-1 (1500 mg/kg) by intravenous injection every 2 days (terminated after 7 days). An uninduced control group (n=5) treated with vehicle was also included. Body weight and DAI score were recorded daily. Mice were sacrificed at day 7, intestines were removed and colon lengths were measured. Colons were then washed with PBS, fixed in formalin solution and histological analysis was performed using H&E staining.

Statistical Analysis

Statistical analyses were performed using Student's t-test. Statistical significance is indicated as *$P<0.05$, $P<0.01$ and *$P<0.001$. Data are presented either as mean±SD of three independent experiments (in vitro experiments) or mean±SEM (in vivo experiments).

Results

To evaluate the effect of YQ23 and TMB-1 in IBD, we employed the DSS-induced acute colitis animal model, a commonly used animal model for the study of IBD, to evaluate the anti-inflammatory effect of the compounds.

(1) Drug Administration—Intraperitoneal Injection

Figure 2A:
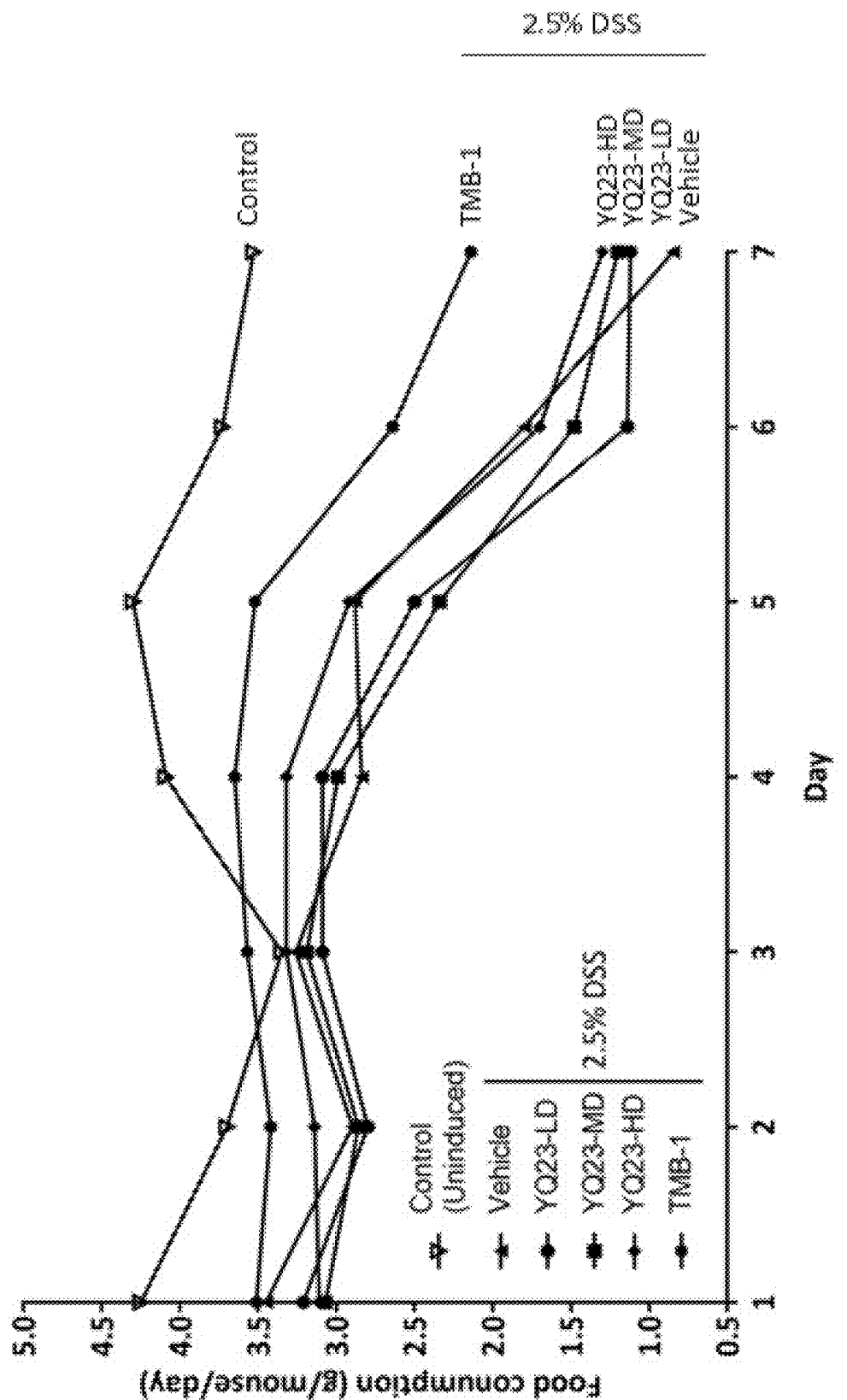
FIG. 2A depicts a graph showing food consumption by mice administered vehicle, YQ23, and TMB-1 over a period of seven days (i.p. injection experiment).
Figure 2B:
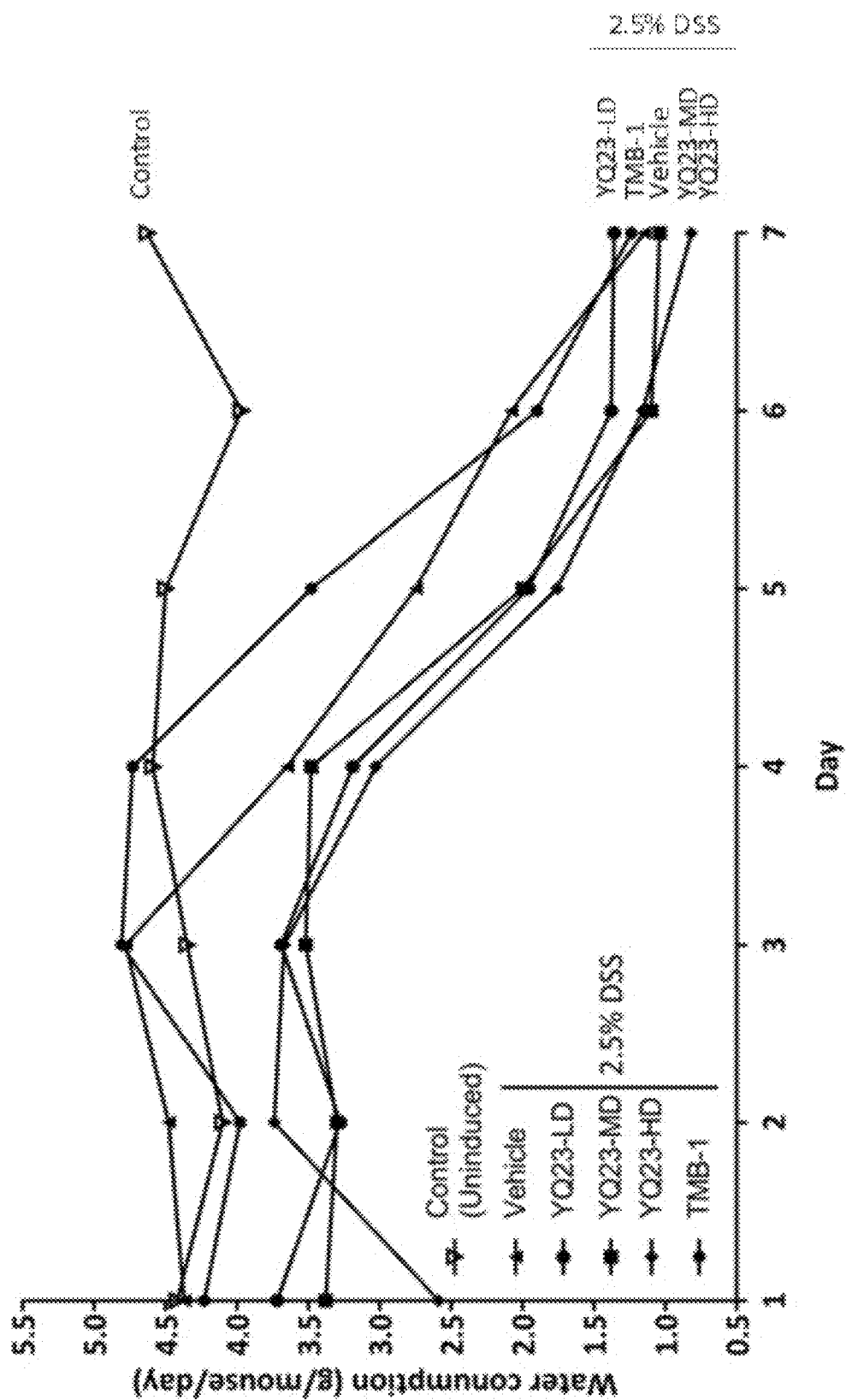
FIG. 2B depicts a graph showing water consumption by mice administered vehicle, YQ23, and TMB-1 over a period of seven days (i.p. injection experiment).
Figure 2C:
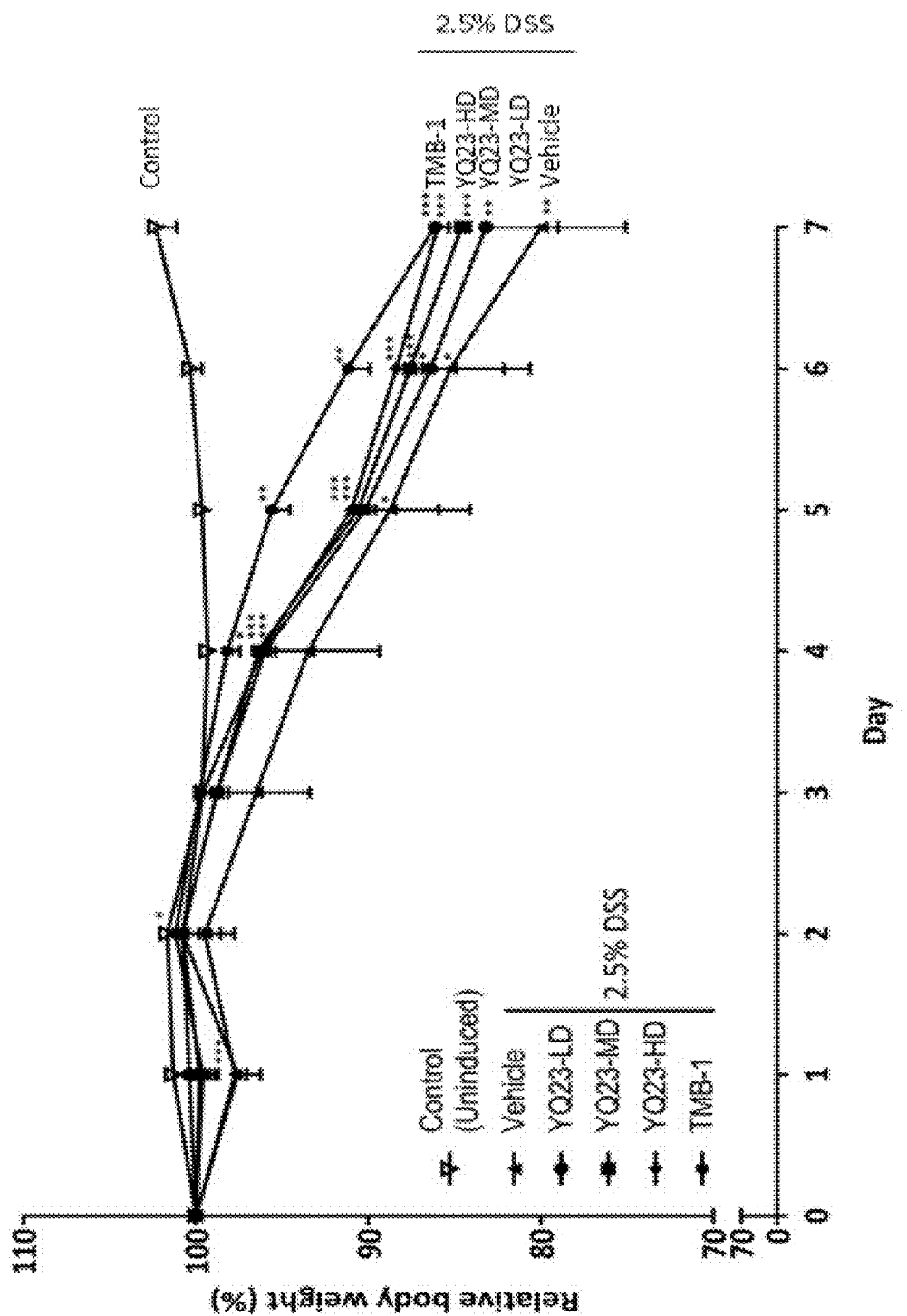
FIG. 2C depicts a graph showing the body weight of mice administered vehicle, YQ23, and TMB-1 over a period of seven days (i.p. injection experiment).

Starting from Day 4 post induction, significant reduction in relative body weights were observed in mice, and a dose-dependent rescuing effect was observed in mice treated with YQ23 (FIG. 2C). At the experimental endpoint, a 20% reduction in body weight was observed in mice treated with vehicle, whereas a 17%, 15%, and 14% reduction was seen in mice treated with YQ23-low dose (LD) (800 mg/kg), YQ23-medium dose (MD) (1,000 mg/kg), and YQ-23-high dose (HD) (1500 mg/kg), respectively. TMB-1 (1,000 mg/kg) exhibited similar effects as YQ23-HD.

Figure 2D:
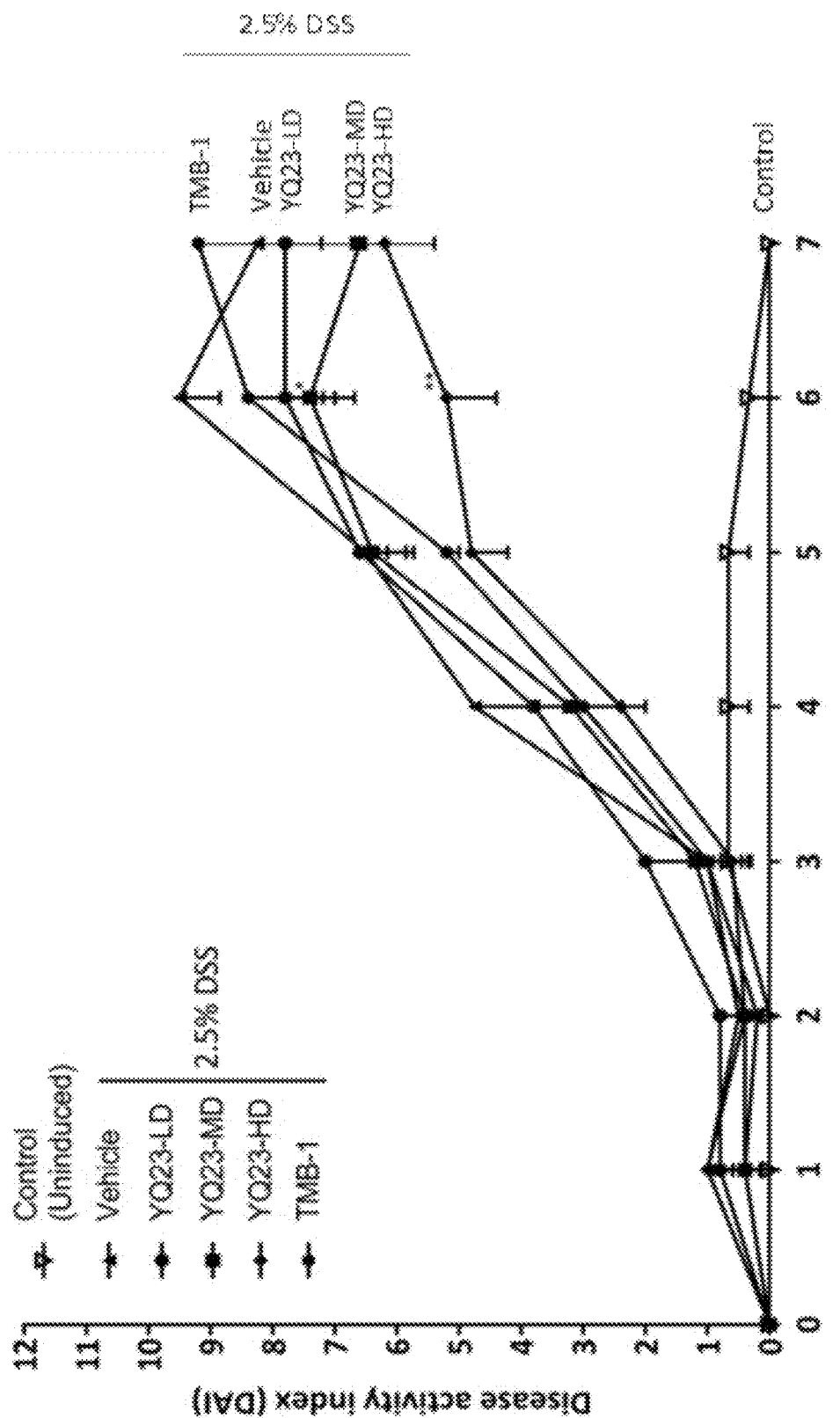
FIG. 2D depicts a graph showing disease activity index (DAI) of mice administered vehicle, YQ23, and TMB-1 over a period of seven days (i.p. injection experiment).

The overall condition of the mice was also evaluated through DAI, a combined score of the relative body weight, stool consistency and fecal blood. As shown in FIG. 2D, mice treated with vehicle exhibited a rapid increase in the DAI score, suggesting the rapid progression of disease. For mice treated with YQ23, again, a dose dependent effect was observed. At the end of the experiment, the average DAI score for vehicle-treated mice was 8.25, in comparison scores were 7.8, 6.6, and 6.2 in mice treated with YQ23-LD, YQ23-MD, and YQ-23-HD respectively (FIG. 2D). In addition, we did not observe significant suppression of food and water consumption in mice treated with different doses of YQ23 or TMB-1 during the experiment (FIGS. 2A-2B).

Figure 2E:
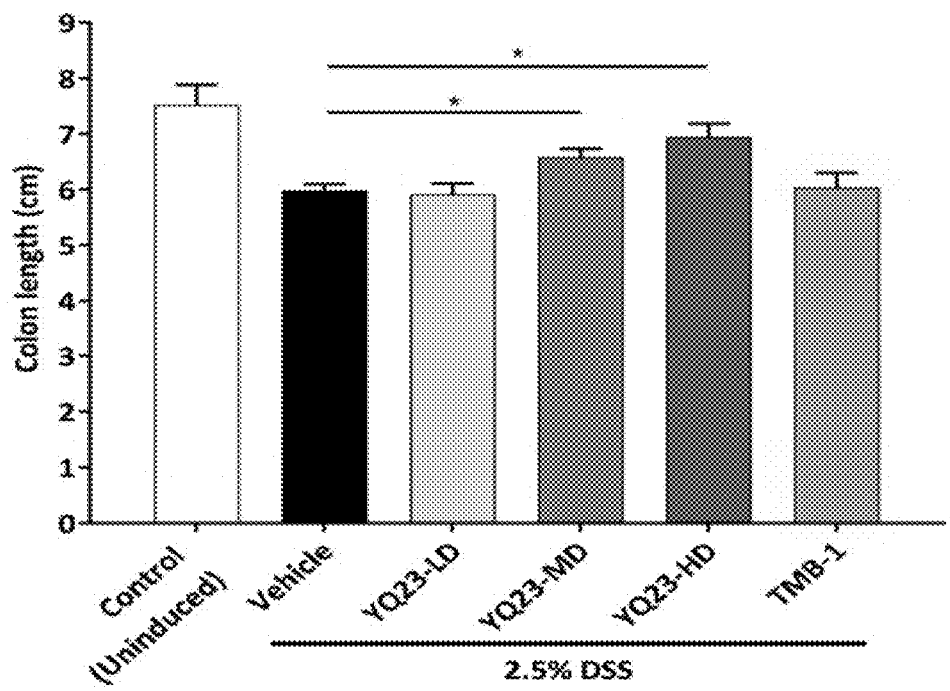
FIG. 2E depicts data for colon length in the IBD models of mice administered vehicle, YQ23, and TMB-1 (i.p. injection experiment).
Figure 2E:
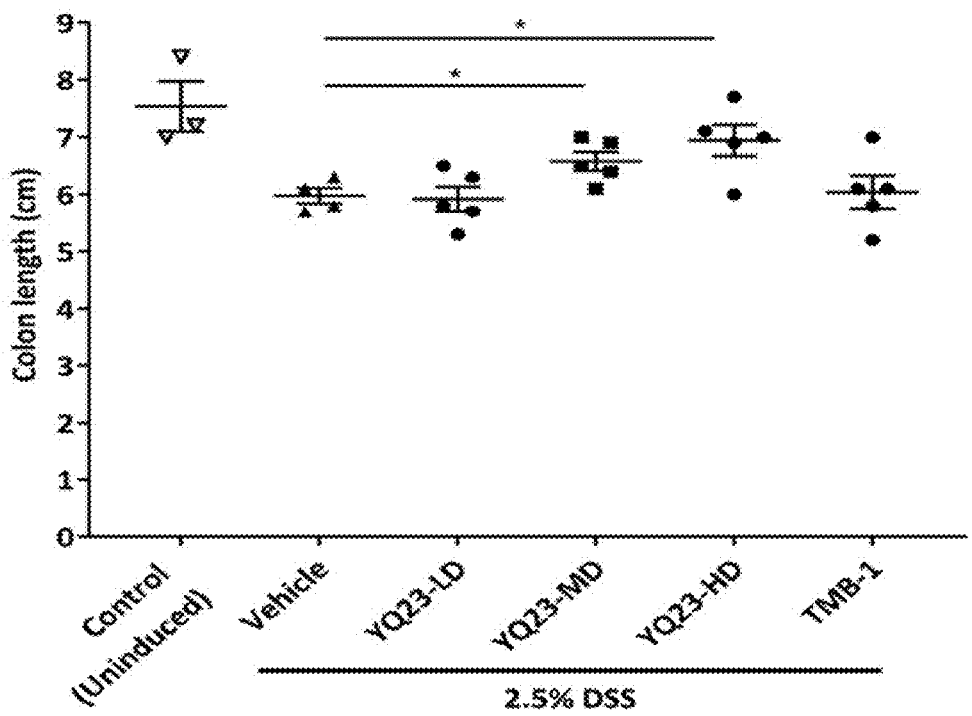
Figure 2F:
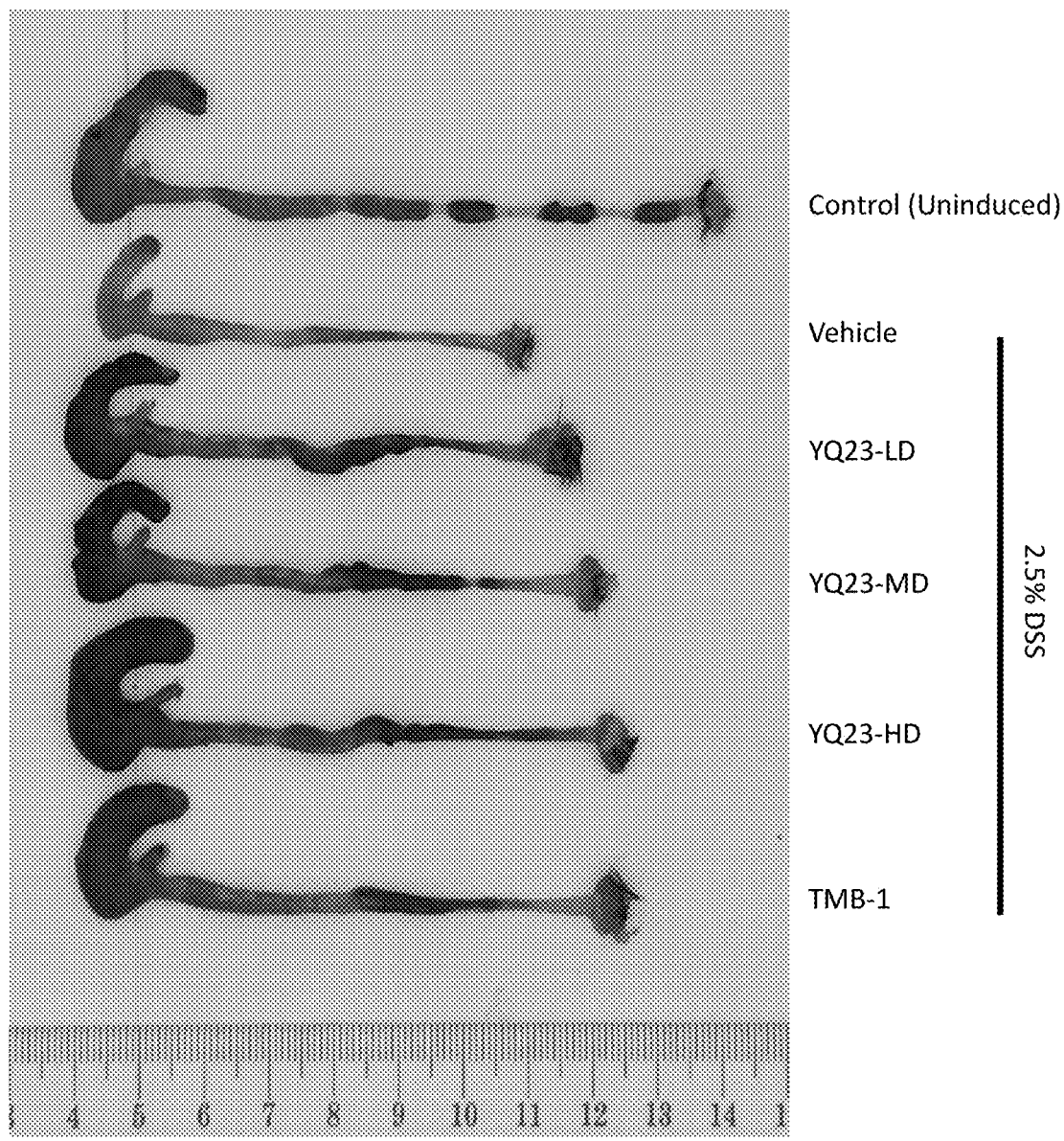
FIG. 2F depicts a picture showing colons isolated from mice in the IBD model administered vehicle, YQ23, and TMB-1 over a period of seven days (i.p. injection experiment).
Figure 2G:
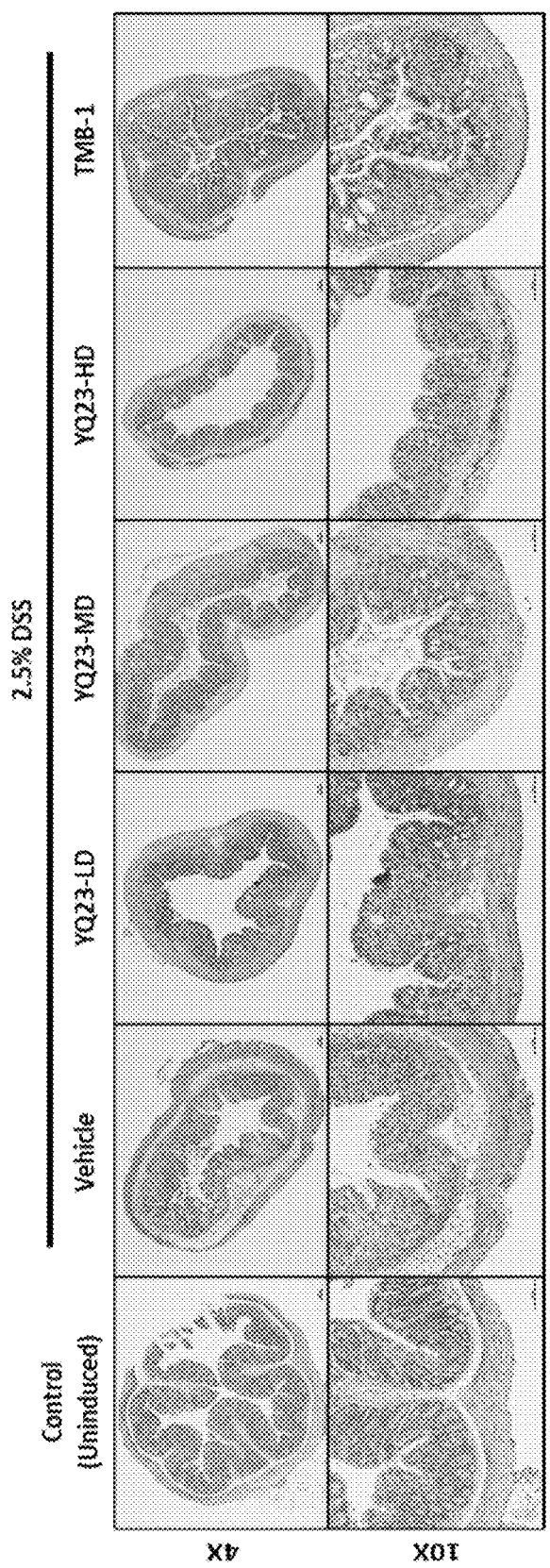
FIG. 2G depicts a picture showing histological analysis performed using H&E staining of colon tissue taken from mice in the IBD model administered vehicle, YQ23, and TMB-1 (i.p. injection experiment).
Figure 2H:
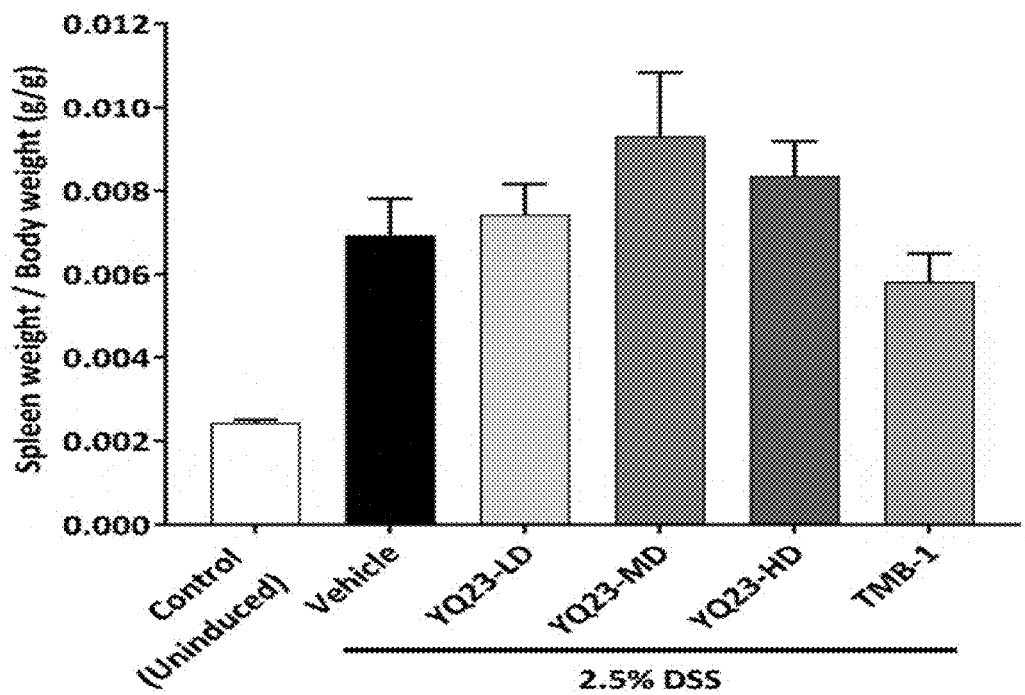
FIG. 2H depicts spleen coefficient data of mice administered vehicle, YQ23, and TMB-1 (i.p. injection experiment).
Figure 2I:
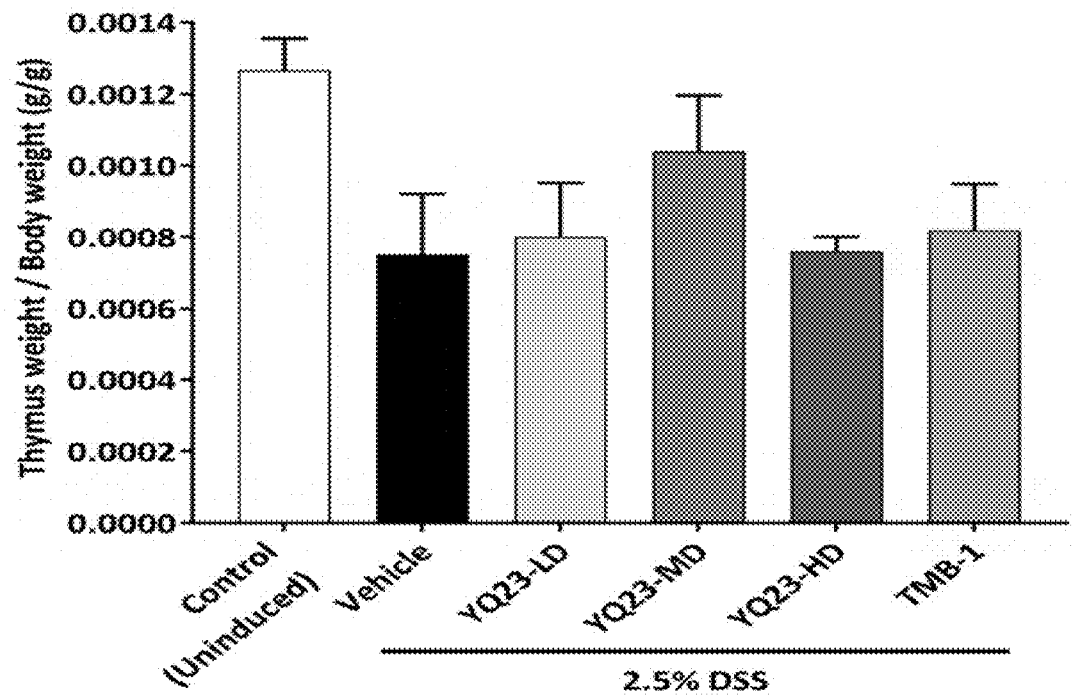
FIG. 2I depicts thymus coefficient data of mice administered vehicle, YQ23, and TMB-1 (i.p. injection experiment).
Figure 2J:
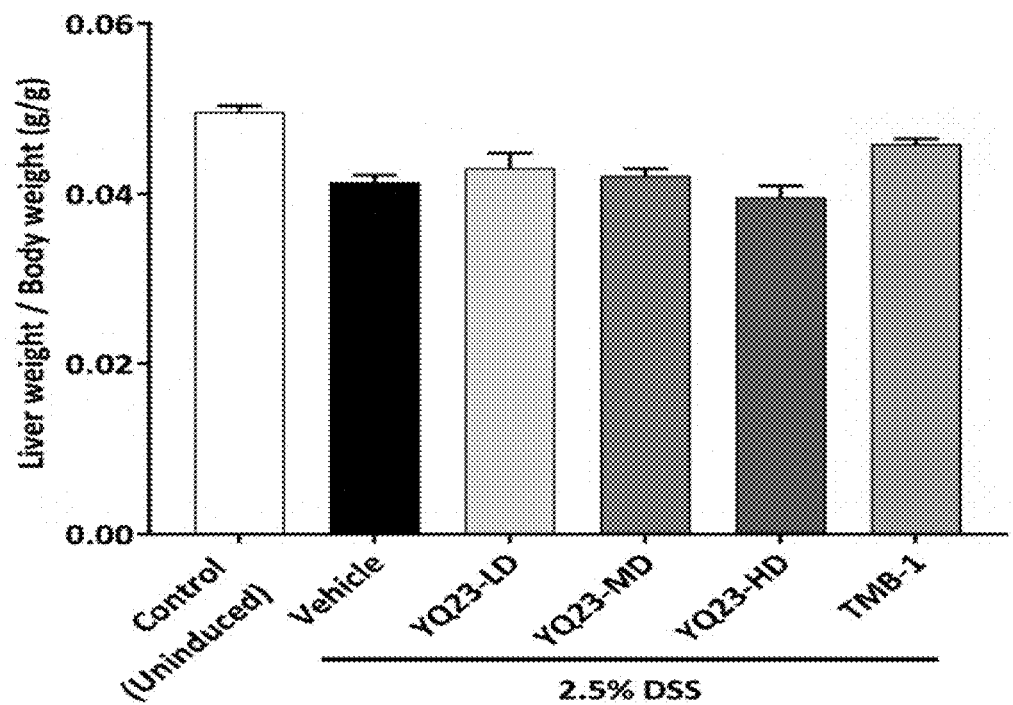
FIG. 2J depicts liver coefficient data of mice administered vehicle, YQ23, and TMB-1 (i.p. injection experiment).
Figure 2K:
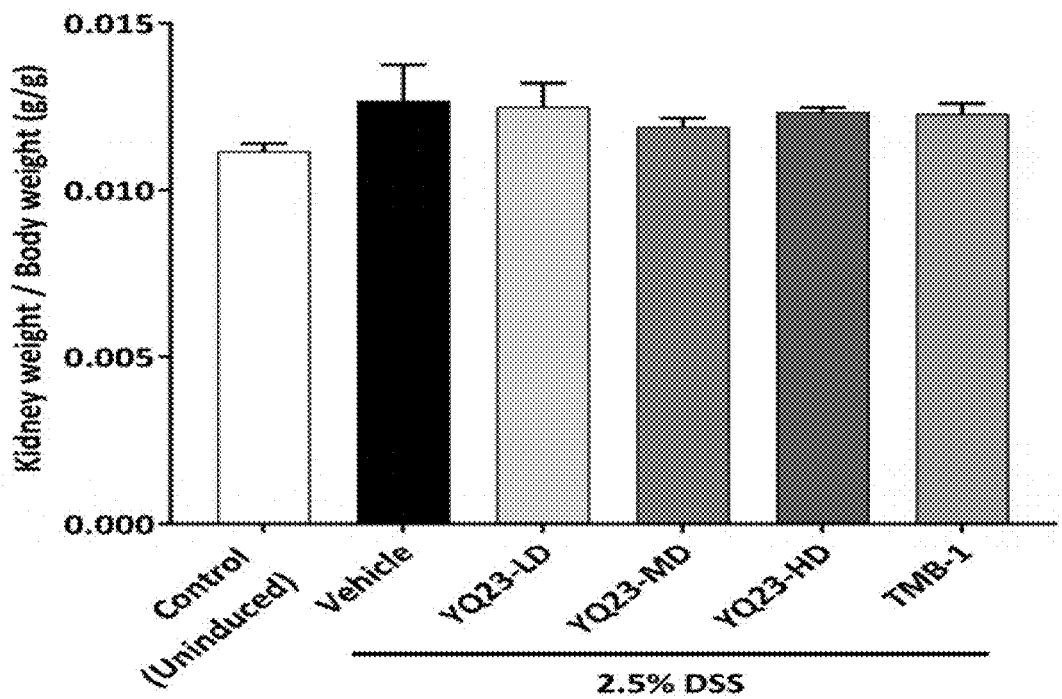
FIG. 2K depicts kidney coefficient data of mice administered vehicle, YQ23, and TMB-1 (i.p. injection experiment).
Figure 2L:
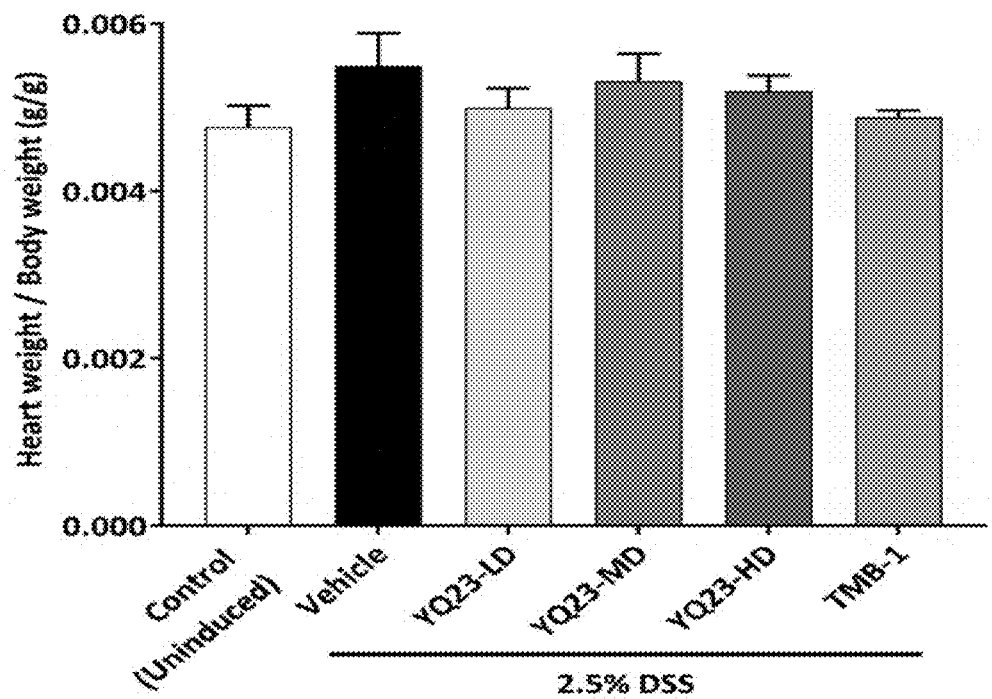
FIG. 2L depicts heart coefficient data of mice administered vehicle, YQ23, and TMB-1 (i.p. injection experiment).
Figure 2M:
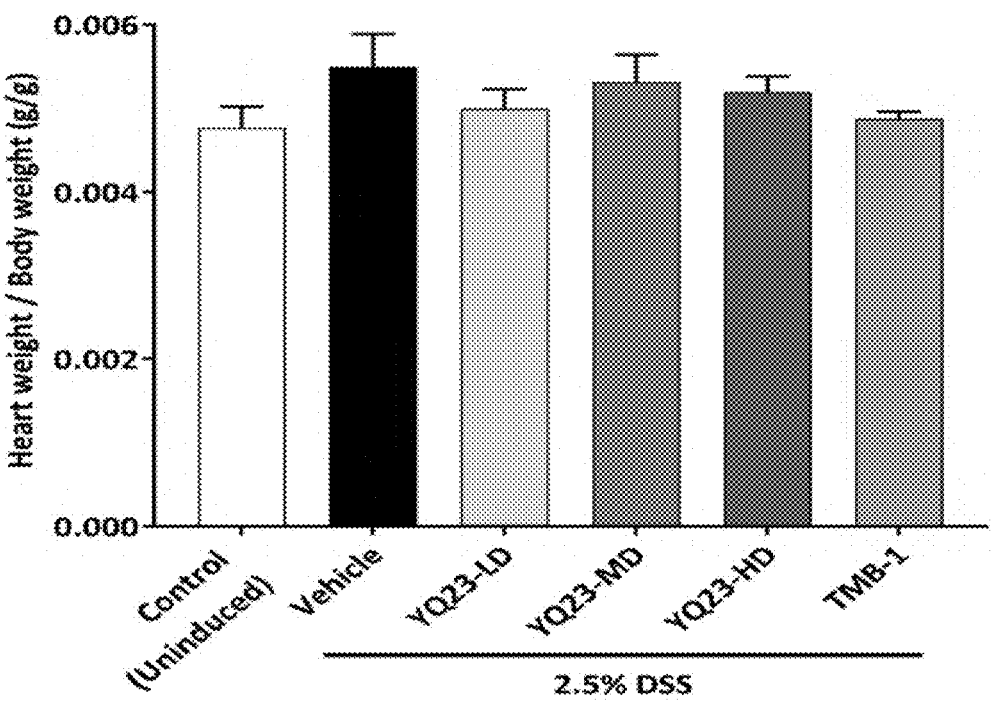
FIG. 2M depicts lung coefficient data of mice administered vehicle, YQ23, and TMB-1 (i.p. injection experiment).

As colon shortening is one of the key features in mice induced with DSS, we examined the colon lengths of DSS-induced mice treated with YQ23. The colon length of mice treated with YQ23-MD or YQ23-HD were increased by 10% and 16% respectively when compared to vehicle-treated mice. TMB-1 only mildly increased the colon length of mice (FIGS. 2E-2F). Histological analysis also showed the beneficial effects of YQ23. Colon sections from DSS-induced mice under vehicle treatment exhibited typical histopathological features of acute colitis, including loss of crypts, inflammatory cell infiltration and destruction of epithelial cell architecture. Treatment with YQ23 or TMB-1 ameliorated the damage induced by DSS, and more importantly, a dose dependent effect was observed in mice treated with YQ23 (FIG. 2G).

We also examined the vital organ (spleen, thymus, liver, kidney, heart and lung) weights and their gross morphology. As shown in FIGS. 2H-2M, no significant alterations in organ weights and organ morphology (data not shown) were observed in mice treated with various doses of YQ23 and TMB-1. Together, our results suggest that YQ23 and TBM-1 could be developed as a potential anti-inflammatory drug, without acute toxicity, for the treatment of IBD.

(2) Drug Administration—Intravenous Injection

Figure 4A:
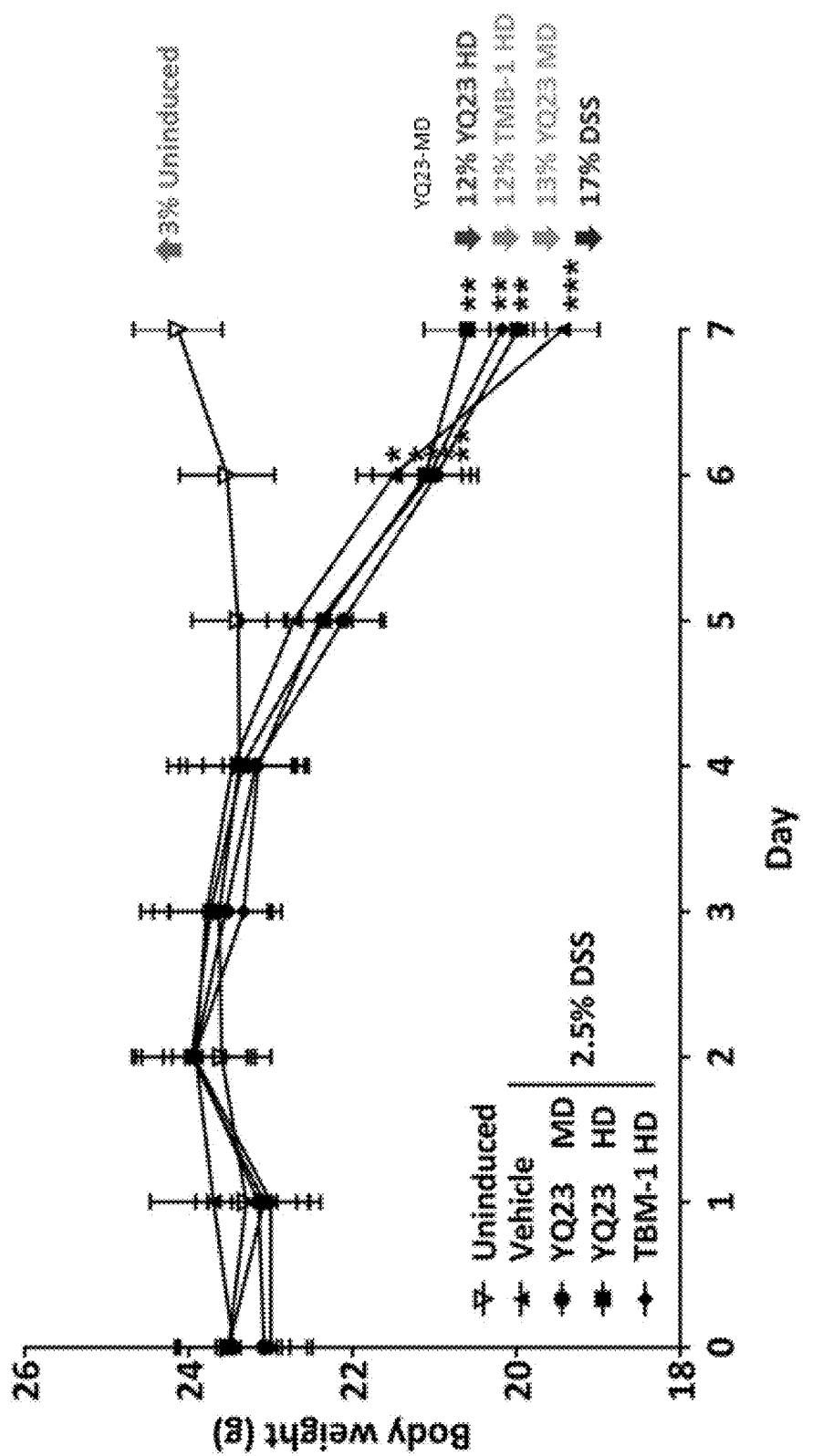
FIG. 4A depicts a graph showing the body weight of mice administered vehicle, YQ23, and TMB-1 over a period of seven days (i.v. injection experiment).

Starting from Day 5 post induction, significant reduction in relative body weights were observed in mice treated with YQ23, TBM-1 and DSS (FIG. 4A). At the experimental endpoint, a 17% reduction in body weight was observed in mice treated with vehicle, whereas a 12%, 12%, and 13% reduction was seen in mice treated with YQ23 (1500 mg/kg), TBM-1 (1500 mg/kg), and YQ23 (1000 mg/kg) respectively, TMB-1 exhibited similar effects as YQ23.

Figure 4B:
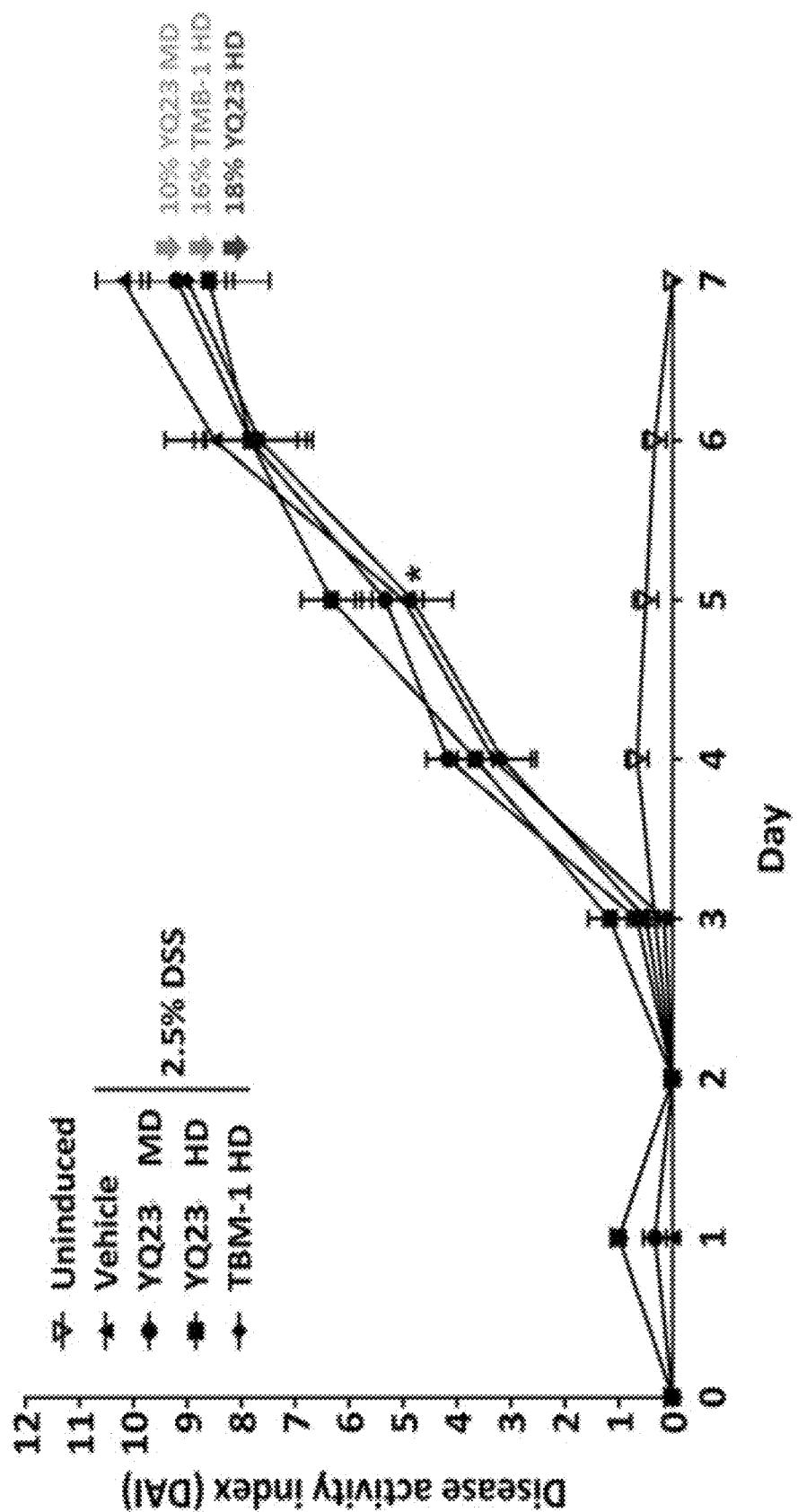
FIG. 4B depicts a graph showing disease activity index (DAI) of mice administered vehicle, YQ23, and TMB-1 over a period of seven days (i.v. injection experiment).

The overall condition of the mice was also evaluated through DAI. As shown in FIG. 4B, mice treated with vehicle exhibited a rapid increase in the DAI score, suggesting the rapid progression of disease. For mice treated with YQ23, again, a dose dependent effect was observed. We observe improvements in mice treated with YQ23 and TMB-1 (FIG. 4B).

Figure 4C:
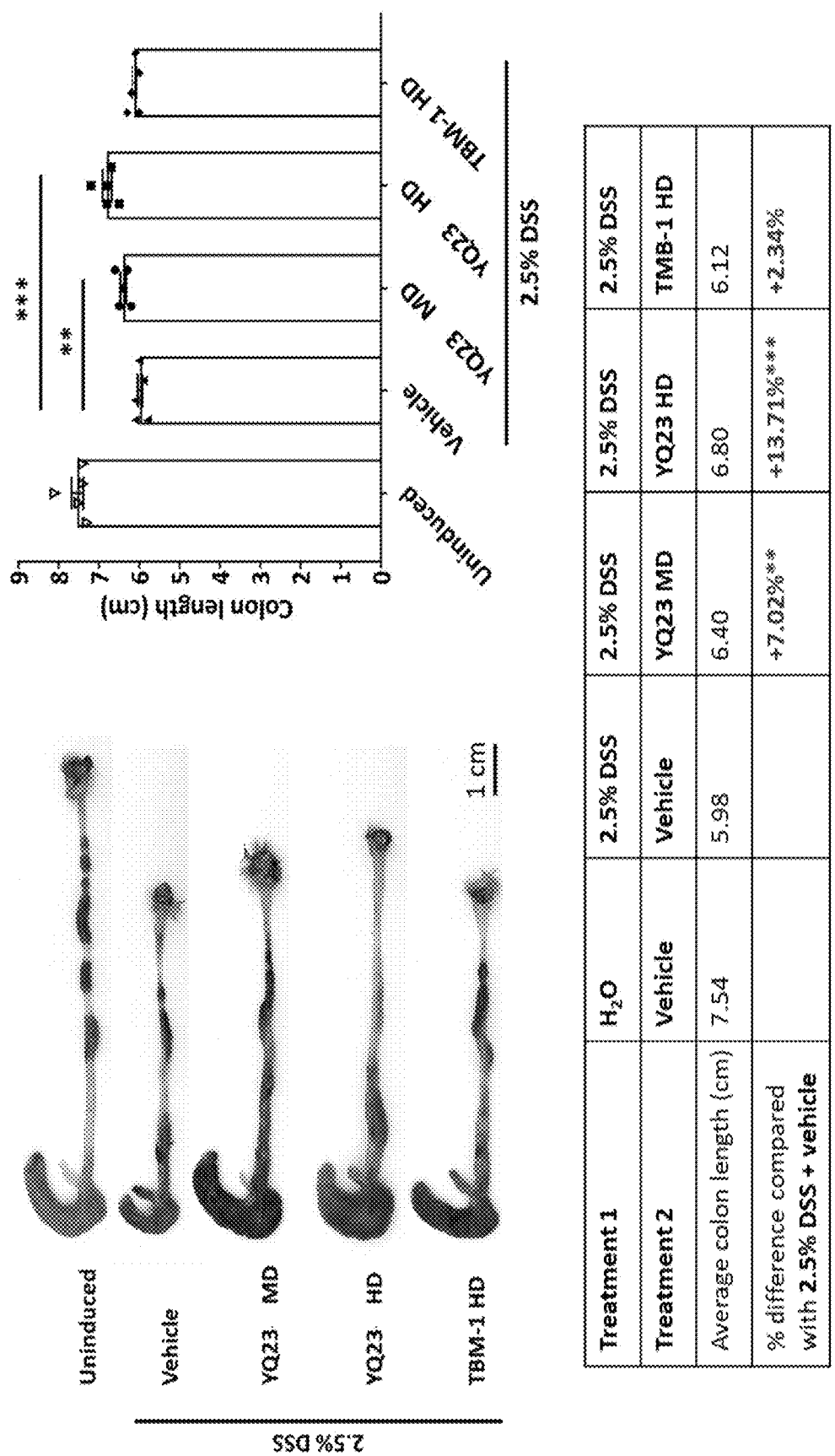
FIG. 4C depicts data for colon length in the IBD models of mice administered vehicle, YQ23, and TMB-1 (i.v. injection experiment).
Figure 4D:
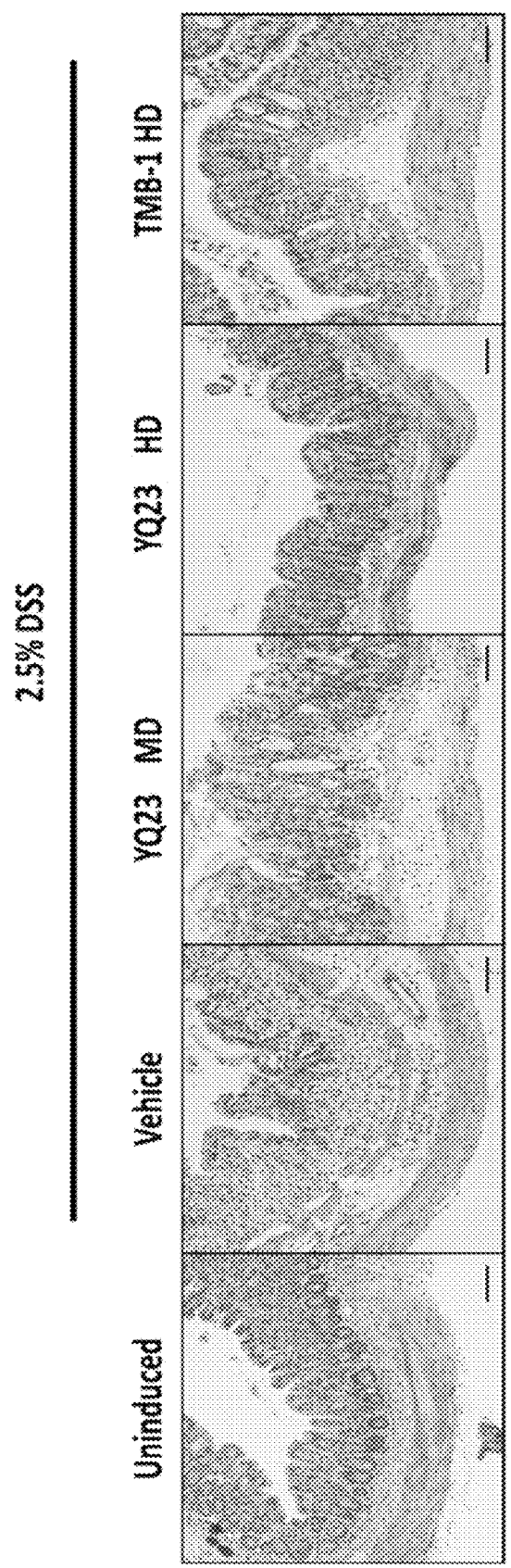
FIG. 4D depicts a picture showing histological analysis performed using H&E staining of colon tissue taken from mice in the IBD model administered vehicle, YQ23, and TMB-1 (i.v. injection experiment).
Figure 4E:
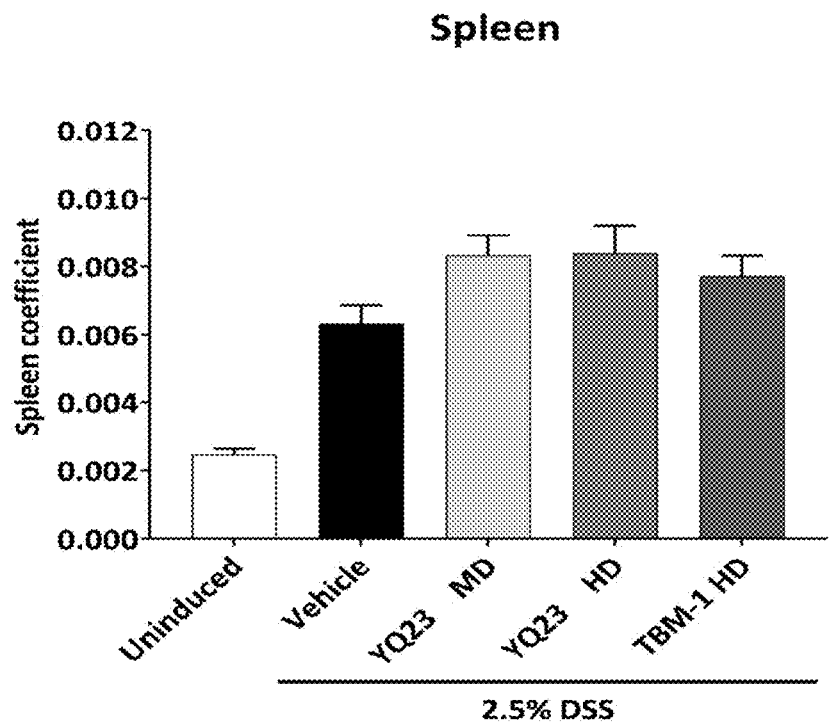
FIG. 4E depicts spleen coefficient data of mice administered vehicle, YQ23, and TMB-1 (i.v. injection experiment).
Figure 4F:
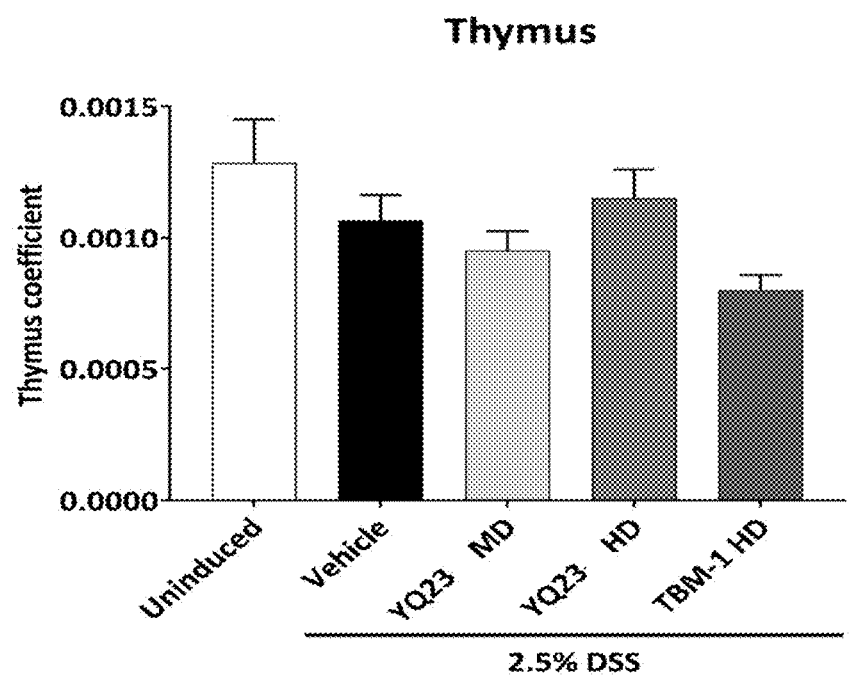
FIG. 4F depicts thymus coefficient data of mice administered vehicle, YQ23, and TMB-1 (i.v. injection experiment).
Figure 4G:
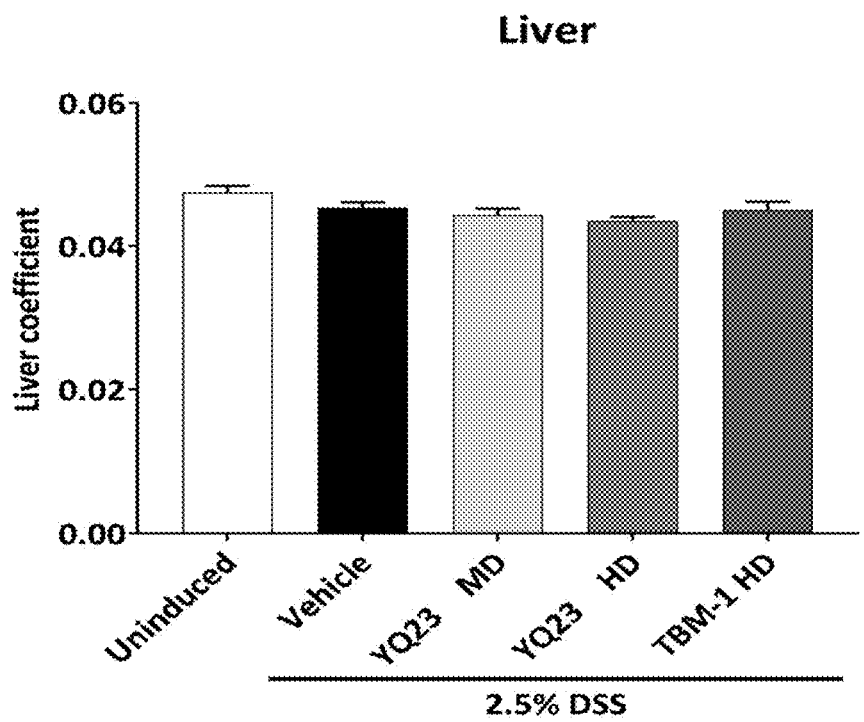
FIG. 4G depicts liver coefficient data of mice administered vehicle, YQ23, and TMB-1 (i.v. injection experiment).

The colon length of mice treated with YQ23 (1000 mg/kg) or YQ23 (1500 mg/kg) or TBM-1 (1500 mg/kg) were increased by 7%, 13.7% and 2.3% respectively when compared to vehicle-treated mice (FIG. 4C). Histological analysis also showed the beneficial effects of YQ23 and TBM-1. Treatment with YQ23 or TMB-1 ameliorated the damage induced by DSS (FIG. 4D).

We also examined the vital organ (spleen, thymus, liver, kidney, heart and lung) weights and their gross morphology. As shown in FIGS. 4E-4J, no significant alterations in organ weights and organ morphology (data not shown) were observed in mice treated with various doses of YQ23 and TMB-1 for i.v. injection.

Discussion

As a chronic, relapsing gastrointestinal inflammatory disorder, the treatment goals for IBD are to induce and maintain remission of symptoms and mucosal inflammation, ultimately improving the quality of life of the IBD patient. At present, 5-ASA and corticosteroids are the major treatment options for IBD. However, side effects and adverse events from these treatments can hinder their therapeutic selection. In the past several years, a host of new treatment options have been developed or are currently in clinical trials, including immunotherapies such as anti-TNF or anti-IL-12/23 antibodies. Although these agents have been shown to be quite effective and safe, they do not treat the underlying cause of the disease and are only effective in a subset of the population. As the incidence and prevalence of IBD continues to rise worldwide, demand for potent, non-toxic and effective therapeutics for treatment of the disease is increasing.

YQ23 is a stabilized nonpolymeric cross-linked tetrameric hemoglobin, which can act as an oxygen carrier. We evaluated the anti-inflammatory effect of YQ23 and the recombinant protein, TMB-1, through utilization of the DSS-induced acute colitis mouse model. This model is a well-established animal model for the study of IBD which mimics the disease manifestation and histopathological characteristics of IBD patients, making it advantageous to other animal models for in vivo studies. Mice under vehicle treatment exhibited typical acute colitis manifestations, including weight loss, shortening of colon length, and increased DAI. Upon treatment of YQ23 and TMB-1, we observed significant improvements in the relative body weight loss, colon shortening, and DAI. Microscopic evaluation of mice colons showed that YQ23 and TMB-1 treatments ameliorated the DSS-induced crypt lost, inflammatory cell infiltration, and destruction of epithelial cell architecture. A dose dependent effect of YQ23 on the above parameters was also observed. Notably, we did not observe any acute toxicity caused by YQ23 and TMB-1 treatments, as mice undergoing YQ23 or TMB-1 treatments did not exhibit reductions in food and water consumption, or alterations in vital organ morphology and weights.

In conclusion, we have provided concrete preliminary data for the development of YQ23 and TMB-1 as anti-inflammatory drugs for the treatment of IBD and other inflammatory diseases.

What is claimed is:

1. A method for treating an inflammatory bowel disease in a subject in need thereof, the method comprising administering a therapeutically effective amount of a hemoglobin to the subject, wherein the hemoglobin is a recombinant hemoglobin comprising a di-alpha chain and two beta chains, wherein the di-alpha chain comprises a polypeptide sequence consisting of SEQ ID NO: 1; and each of the two beta chains comprise a polypeptide sequence consisting of SEQ ID NO: 2, and wherein the hemoglobin has an oxygen p50 value between 20 and 50 mmHg.

2. The method of claim 1, wherein the inflammatory bowel disease is selected from the group consisting of ulcerative colitis, indeterminate colitis, Crohn's disease, lymphocytic colitis, microscopic colitis, collagenous colitis, autoimmune enteropathy, allergic gastrointestinal disease, and eosinophilic gastrointestinal disease.

3. The method of claim 1, wherein the inflammatory bowel disease is selected from the group consisting of ulcerative colitis, Crohn's disease, and indeterminate colitis.

4. The method of claim 1, wherein the inflammatory bowel disease is Crohn's disease.

5. The method of claim 1, wherein the inflammatory bowel disease is ulcerative colitis.

6. The method of claim 1, wherein the subject has a circulating hemoglobin concentrations between 12-15 g/dl or greater.

7. The method. of claim 1, wherein the hemoglobin is administered intraperitoneally.

8. The method of claim 1, wherein the hemoglobin is administered intravenously.

9. The method of claim wherein the hemoglobin has an oxygen p50 value greater than 24 mm Hg, and less than 50 mm Hg.

10. The method of claim 1, wherein the hemoglobin has an oxygen p50 value greater than 30 mm Hg and less than 50 Hg.

11. The method of claim 1 further comprising co-administering a therapeutically effective amount of at least one agent to the subject, wherein the at least one agent is selected from the group consisting of an anti-inflammatory agent and an antibacterial agent.

* * * * *

UNITED STATES PATENT AND TRADEMARK OFFICE
CERTIFICATE OF CORRECTION

PATENT NO. : 11,535,655 B2  
APPLICATION NO. : 17/247223  
DATED : December 27, 2022  
INVENTOR(S) : Sui Yi Kwok, Norman Fung Man Wai and Chi Shing Tai Page 1 of 2

It is certified that error appears in the above-identified patent and that said Letters Patent is hereby corrected as shown below:

In the Drawings

Figures 3A, 3B:
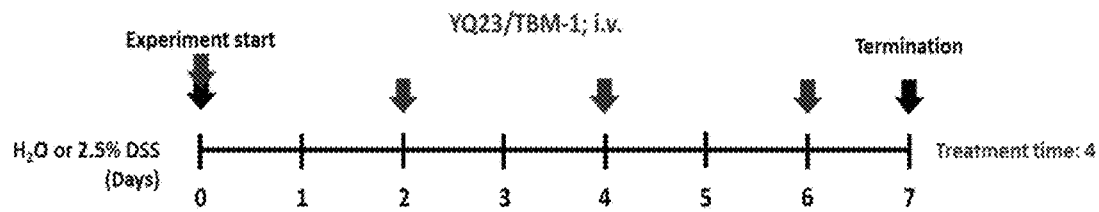
FIG. 3A depicts an exemplary treatment regimen according to certain embodiments described herein (i.v. injection experiment).
FIG. 3B depicts a table showing dosage amounts of YQ23 and TMB-1 for experiments described below (i.v. injection experiment).

Sheet 1, Figure 1A, "TMB-1" should read --TBM1--.
Sheet 1, Figure 1B, both instances of "TMB-1" should each read --TBM1--.
Sheet 2, Figure 2A, both instances of "TMB-1" should each read --TBM1--.
Sheet 3, Figure 2B, both instances of "TMB-1" should each read --TBM1--.
Sheet 4, Figure 2C, both instances of "TMB-1" should each read --TBM1--.
Sheet 5, Figure 2D, both instances of "TMB-1" should each read --TBM1--.
Sheet 6, Figure 2E, both instances of "TMB-1" should each read --TBM1--.
Sheet 7, Figure 2E, "TMB-1" should read --TBM1--.
Sheet 8, Figure 2F, "TMB-1" should read --TBM1--.
Sheet 9, Figure 2G, "TMB-1" should read --TBM1--.
Sheet 10, Figure 2H, "TMB-1" should read --TBM1--.
Sheet 10, Figure 2I, "TMB-1" should read --TBM1--.
Sheet 11, Figure 2J, "TMB-1" should read --TBM1--.
Sheet 11, Figure 2K, "TMB-1" should read --TBM1--.
Sheet 12, Figure 2L, "TMB-1" should read --TBM1--.
Sheet 12, Figure 2M, "TMB-1" should read --TBM1--.
Sheet 13, Figure 3A, "TBM-1" should read --TBM1--.
Sheet 13, Figure 3B, both instances of "TBM-1" should each read --TBM1--.
Sheet 14, Figure 4A, "TBM-1" should read --TBM1--.
Sheet 14, Figure 4A, "TMB-1" should read --TBM1--.
Sheet 15, Figure 4B, "TBM-1" should read --TBM1--.
Sheet 15, Figure 4B, "TMB-1" should read --TBM1--.
Sheet 16, Figure 4C, both instances of "TBM-1" should each read --TBM1--.
Sheet 16, Figure 4C, "TMB-1" should read --TBM1--.
Sheet 17, Figure 4D, "TMB-1" should read --TBM1--.
Sheet 18, Figure 4E, "TBM-1" should read --TBM1--.
Sheet 18, Figure 4F, "TBM-1" should read --TBM1--.
Sheet 19, Figure 4G, "TBM-1" should read --TBM1--.

Signed and Sealed this  
Eighteenth Day of April, 2023

Katherine Kelly Vidal  
*Director of the United States Patent and Trademark Office*

CERTIFICATE OF CORRECTION (continued)
U.S. Pat. No. 11,535,655 B2

Figure 4H:
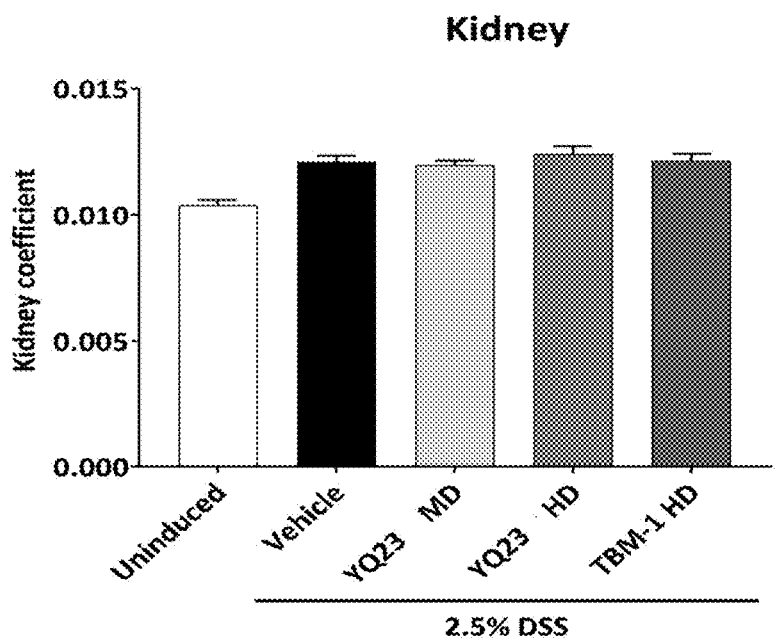
FIG. 4H depicts kidney coefficient data of mice administered vehicle, YQ23, and TMB-1 (i.v. injection experiment).
Figure 4I:
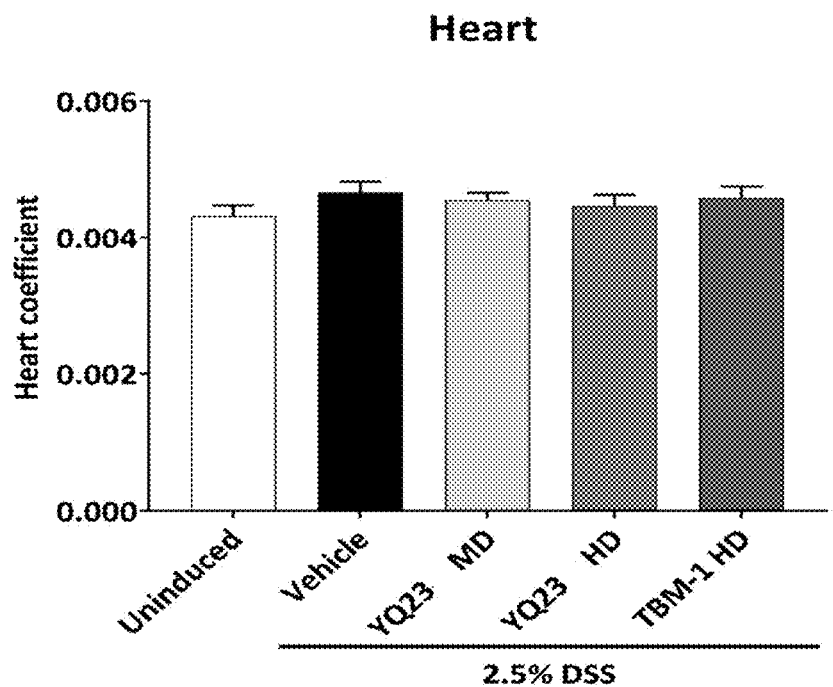
FIG. 4I depicts heart coefficient data of mice administered vehicle, YQ23, and TMB-1 (i.v. injection experiment).
Figure 4J:
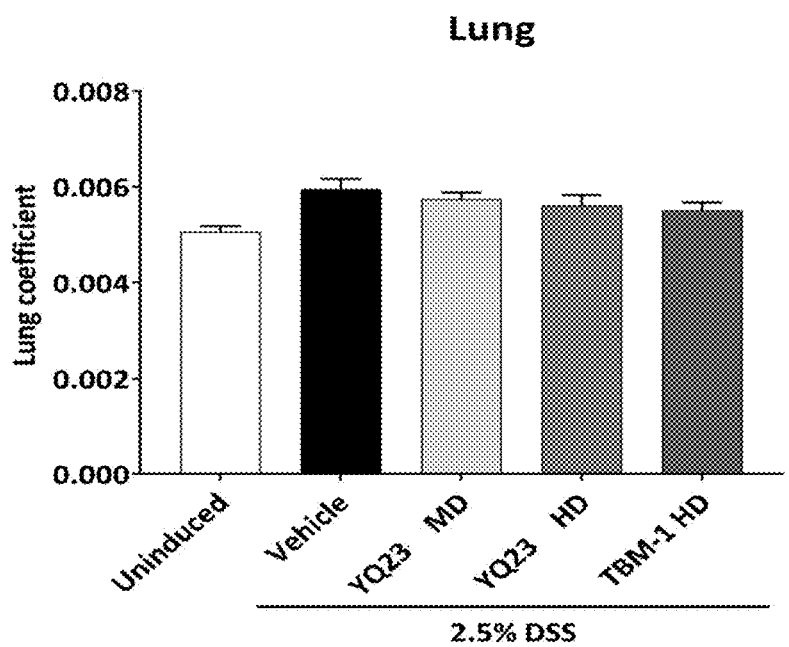
FIG. 4J depicts lung coefficient data of mice administered vehicle, YQ23, and TMB-1 (i.v. injection experiment).

Sheet 19, Figure 4H, "TBM-1" should read --TBM1--.
Sheet 20, Figure 4I, "TBM-1" should read --TBM1--.
Sheet 20, Figure 4J, "TBM-1" should read --TBM1--.

In the Specification

In Column 1, Line 48, "TMB-1" should read --TBM1--; and Line 53, "TBM-1" should read --TBM1--.
In Column 3, Line 26, "TMB-1" should read --TBM1--; Line 29, "TMB-1" should read --TBM1--; Line 32, "TMB-1" should read --TBM1--; Line 35, "TMB-1" should read --TBM1--; Line 39, "TMB-1" should read --TBM1--; Line 42, "TMB-1" should read --TBM1--; Line 46, "TMB-1" should read --TBM1--; Line 51, "TMB-1" should read --TBM1--; Line 53, "TMB-1" should read --TBM1--; Line 55, "TMB-1" should read --TBM1--; Line 57, "TMB-1" should read --TBM1--; Line 59, "TMB-1" should read --TBM1--; Line 62, "TMB-1" should read --TBM1--; and Line 64, "TMB-1" should read --TBM1--.
In Column 4, Line 2, "TMB-1" should read --TBM1--; Line 5, "TMB-1" should read --TBM1--; Line 8, "TMB-1" should read --TBM1--; Line 11, "TMB-1" should read --TBM1--; Line 16, "TMB-1" should read --TBM1--; and Line 18, "TMB-1" should read --TBM1--.
In Column 4, Line 20, "TMB-1" should read --TBM1--; Line 23, "TMB-1" should read --TBM1--; Line 25, "TMB-1" should read --TBM1--; Line 28, "TMB-1" should read --TBM1--; Line 30, "TMB-1" should read --TBM1--; Line 32, "TMB-1" should read --TBM1--; and Line 34, "TMB-1" should read --TBM1--.
In Column 7, Line 6, "rom" should read --from--.
In Column 11, Line 63, "TBM-1" should read --TBM1--; Line 65, "TBM-1" should read --TBM1--; and Line 66, "TMB-1" should read --TBM1--.
In Column 12, Line 23, "TMB-1" should read --TBM1--; Line 49, "TMB-1" should read --TBM1--; and Line 64, "TMB-1" should read --TBM1--.
In Column 13, Line 11, "TMB-1" should read --TBM1--; Line 27, "TMB-1" should read --TBM1--; Line 34, "TMB-1" should read --TBM1--; Line 41, "TMB-1" should read --TBM1--; Line 50, "TMB-1" should read --TBM1--; Line 50, "TBM-1" should read --TBM1--; Line 57, "TBM-1" should read --TBM1--; Line 62, "TBM-1" should read --TBM1--; and Line 63, "TMB-1" should read --TBM1--.
In Column 14, Line 3, "TMB-1" should read --TBM1--; Line 5, "TBM-1" should read --TBM1--; Line 8, "TBM-1" should read --TBM1--; Line 9, "TMB-1" should read --TBM1--; Line 16, "TMB-1" should read --TBM1--; Line 42, "TMB-1" should read --TBM1--; Line 50, "TMB-1" should read --TBM1--; Line 54, "TMB-1" should read --TBM1--; Line 59, "TMB-1" should read --TBM1--; Line 60, "TMB-1" should read --TBM1--; and Line 64, "TMB-1" should read --TBM1--.